(12) United States Patent
Daily et al.

(10) Patent No.: US 12,320,811 B2
(45) Date of Patent: Jun. 3, 2025

(54) METHODS OF DETECTING CANCER

(71) Applicant: Ascendant Diagnostics, LLC, Springdale, AR (US)

(72) Inventors: Anna Daily, Fayetteville, AR (US); Lindsay Rutherford, Fayetteville, AR (US)

(73) Assignee: Ascendant Diagnostics, LLC, Springdale, AR (US)

( * ) Notice: Subject to any disclaimer, the term of this patent is extended or adjusted under 35 U.S.C. 154(b) by 0 days.

(21) Appl. No.: 17/717,985

(22) Filed: Apr. 11, 2022

(65) Prior Publication Data

US 2023/0228753 A1 Jul. 20, 2023

Related U.S. Application Data

(63) Continuation of application No. 16/356,879, filed on Mar. 18, 2019, now abandoned, which is a continuation of application No. 14/879,982, filed on Oct. 9, 2015, now Pat. No. 10,451,625, which is a continuation-in-part of application No. 14/707,089, filed on May 8, 2015, now Pat. No. 10,613,090.

(60) Provisional application No. 62/061,900, filed on Oct. 9, 2014, provisional application No. 61/991,061, filed on May 9, 2014.

(51) Int. Cl.
| | |
|---|---|
| G01N 33/574 | (2006.01) |
| C12Q 1/6886 | (2018.01) |
| G01N 30/72 | (2006.01) |
| H01J 49/00 | (2006.01) |
| H01J 49/40 | (2006.01) |

(52) U.S. Cl.
CPC ..... *G01N 33/57415* (2013.01); *C12Q 1/6886* (2013.01); *G01N 30/7233* (2013.01); *G01N 33/57488* (2013.01); *G01N 33/57496* (2013.01); *C12Q 2600/158* (2013.01); *H01J 49/00* (2013.01); *H01J 49/40* (2013.01)

(58) Field of Classification Search
CPC .......... C12Q 1/6886; C12Q 2600/158
See application file for complete search history.

(56) References Cited

U.S. PATENT DOCUMENTS

| | | |
|---|---|---|
| 7,662,580 B2 | 2/2010 | Georges et al. |
| 7,951,529 B2 | 5/2011 | Li et al. |
| 10,451,625 B2 | 10/2019 | Daily et al. |
| 10,613,090 B2 | 4/2020 | Daily et al. |
| 2004/0029114 A1 | 2/2004 | Mack et al. |
| 2006/0019256 A1 | 1/2006 | Clarke et al. |
| 2009/0035801 A1 | 2/2009 | Goldknopf et al. |
| 2009/0215102 A1 | 8/2009 | Moses et al. |
| 2010/0184049 A1 | 7/2010 | Goodison et al. |
| 2010/0190656 A1 | 7/2010 | Li et al. |
| 2011/0008914 A1 | 1/2011 | Yeung et al. |
| 2011/0212851 A1 | 9/2011 | Wong et al. |
| 2012/0171221 A1 | 7/2012 | Hamm-Alvarez et al. |
| 2012/0183555 A1 | 7/2012 | Chang et al. |
| 2013/0217057 A1 | 8/2013 | Kearney et al. |
| 2014/0186332 A1 | 7/2014 | Ezrin et al. |
| 2014/0213467 A1 | 7/2014 | Yeung |
| 2015/0141273 A1 | 5/2015 | Bosch et al. |
| 2016/0003786 A1 | 1/2016 | Daily et al. |
| 2016/0161492 A1 | 6/2016 | Daily et al. |
| 2019/0277851 A1 | 9/2019 | Daily et al. |

FOREIGN PATENT DOCUMENTS

| | | |
|---|---|---|
| CA | 2875418 A1 | 6/2015 |
| CN | 101484803 A | 7/2009 |
| CN | 104805197 A | 7/2015 |
| WO | WO-9835229 A1 | 8/1998 |
| WO | WO-0113117 A2 | 2/2001 |
| WO | WO-0171357 A2 | 9/2001 |
| WO | WO-2008014458 A2 | 1/2008 |
| WO | WO-2008054764 A2 | 5/2008 |
| WO | WO-2009097692 A1 | 8/2009 |
| WO | WO-2010053816 A2 | 5/2010 |
| WO | WO-2011100472 A1 | 8/2011 |
| WO | WO-2012116979 A1 | 9/2012 |
| WO | WO-2013106913 A1 | 7/2013 |
| WO | WO-2013154422 A1 | 10/2013 |
| WO | WO-2013186639 A2 | 12/2013 |
| WO | WO-2014133855 A1 | 9/2014 |

OTHER PUBLICATIONS

Kondo et al, Acta Med Okayama 56:31-34, 2002.*
Sakaguchi et al, Amino Acids, 41:797-807, 2011.*
Mandelson et al, J Natl Cancer Inst 92:1081-1087, 2000.*
Armstrong et al., "Breast Cancer Risk Prediction and Mammagraphy Biopsy Decisions, a Model Based Study," Am J Prev Med 44(1):15-22 (2013).
Böhm et al., "Serum proteome profiling of primary breast cancer indicates a specific biomarker profile," Oncology Reports 26:1051-1056 (2011).
Bigenwald et al., "Is Mammography Adequate for Screening Women with Inherited BRCA Mutations and Low Breast Density?," Cancer Epidemiol Biomarkers Prev 17(3): 706-711 (2008).
Bohm D., et al., "Comparison of Tear Protein Levels in Breast Cancer Patients and Healthy Controls Using a De Novo Proteomic Approach," Oncology Reports, Aug. 2012, vol. 28(2), pp. 429-438.
Braidotti, et al., "DMBT1 expression is down-regulated in breast cancer." BMC Cancer (2004); 4: 46, 9 pages.

(Continued)

*Primary Examiner* — Mark Halvorson
(74) *Attorney, Agent, or Firm* — COOLEY LLP

(57) ABSTRACT

Method and kits for detecting cancer, and in particular breast cancer, in a subject by measuring the levels of at least one of a series of biomarkers, as compared to a control sample lacking cancer. The expression of the biomarker either increases or decreases in samples from subjects with cancer, as compared to the expression level in subjects without cancer. The sample is optimally an ocular sample, such as an isolated tear sample or ocular wash, but can also be from saliva, or other bodily fluid. Kits can include a collection tube and protease inhibitors or protein stabilizers.

16 Claims, 17 Drawing Sheets

Specification includes a Sequence Listing.

(56) References Cited

OTHER PUBLICATIONS

Braun, Michael, et al. "Down-regulation of microfilamental network-associated proteins in leukocytes of breast cancer patients: potential application to predictive diagnosis." Cancer Genomics-Proteomics 6.1: 31-40 (2009).
Brown et al., "Screening Mammography in Community Practice: Positive Predictive Value of Abnormal Findings and Yield of Follow-Up Diagnostic Procedures," AJR 165:1373-1377 (Dec. 1995).
Bundred, et al., "Is apocrine differentiation in breast carcinoma of prognostic significance?" British Journal of Cancer (1990); 62: 113-117.
Cafferey, B.E., "Sjogren's Syndrome: A Clinical and Biochemical Analysis." Thesis 2009; Waterloo, Ontario, Canada, 248 pages.
Cancemi, Patrizia, et al. "Large-scale proteomic identification of S100 proteins in breast cancer tissues." BMC Cancer 10.1: 476 (2010).
Catanzaro, et al., "Oncogenic Ras induces inflammatory cytokine production by upregulating the squamous cell carcinoma antigens SerpinB3/B4." Nature Communications (2014); Article No. 3729 (2014), 12 pages.
Celis, Julio E., et al. "Molecular pathology of breast apocrine carcinomas: a protein expression signature specific for benign apocrine metaplasia." FEBS Letters 580.12: 2935-2944 (2006).
Chen, Xiang, et al. "Comparative profiling of triple-negative breast carcinomas tissue glycoproteome by sequential purification of glycoproteins and stable isotope labeling." Cellular Physiology and Biochemistry 38.1: 110-121 (2016).
Colak, Dilek, et al. "Age-specific gene expression signatures for breast tumors and cross-species conserved potential cancer progression markers in young women." PLOS ONE 8.5: e63204 (2013).
Cross, S. S., et al. "Expression of S100 proteins in normal human tissues and common cancers using tissue microarrays: S100A6, S100A8, S100A9 and S100A11 are all overexpressed in common cancers." Histopathology 46.3: 256-269 (2005).
Do, et al., "Associations between the Expression of Mucins (MUC1, MUC2, MUC5AC, and MUC6) and Clinicopathologic Parameters of Human Breast Ductal Carcinomas." J Breast Cancer (2013); 16(2) 152-158.
Esmaeli, B., et al., "Docetaxel Secretion in Tears Association With Lacrimal Drainage Obstruction." Arch Ophthalmol. (2002); 120(9): 1180-1182.
European Patent Application No. 16168524.3, Extended European Search Report dated Feb. 6, 2017, 22 pages.
European Patent Application No. 16168524.3, Partial European Search Report dated Oct. 24, 2016, 9 pages.
Freije, et al., "Human Zn-α2-glycoprotein cDNA cloning and expression analysis in benign and malignant breast tissues." FEBS Letters (1991); 290(1-2): 247-249.
Fusco, Ornella, et al. "90K (MAC-2 Bp) gene expression in breast cancer and evidence for the production of 90K by peripheral-blood mononuclear cells." International Journal of Cancer 79.1: 23-26 (1998).
Grady, D., "Study of Breast Biopsies Finds Surgery Used Too Extensively," The New York Times (4 pages) (Feb. 18, 2011).
Gunaldi, Meral, et al. "Diagnostic importance of S100A9 and S100A12 in breast cancer." Biomedicine & Pharmacotherapy 76: 52-56 (2015).
Iacobelli, S., et al. "Prognostic value of a novel circulating serum 90K antigen in breast cancer." British Journal of Cancer 69.1: 172-176 (1994).
Klifa et al., "Magnetic resonance imaging for secondary assessment of breast density in a high-risk cohort," Magnetic Resonance Imaging 28(1):8-15 (2010).
Kolb et al., "Comparison of the Performance of Screening Mammography, Physical Examination, and Breast US and Evaluation of Factors that Influence Them: An Analysis of 27,825 Patient Evaluations," Radiology 225(1):165-175 (2002).
Kormelink, Tom Groot, et al. "Immunoglobulin free light chains are biomarkers of poor prognosis in basal-like breast cancer and are potential targets in tumor-associated inflammation." Oncotarget 5.10: 3159-3167 (2014).
Koths, K., et al. "Cloning and characterization of a human Mac-2-binding protein, a new member of the superfamily defined by the macrophage scavenger receptor cysteine-rich domain." Journal of Biological Chemistry 268.19: 14245-14249 (1993).
Lebrecht et al., "Diagnosis of Breast Cancer by Tear Proteomic pattern," Cancer Genomics & Proteomics 6(3):177-182 (2009b).
Lebrecht et al., "Surface-enhanced Laser Desorption/Ionisation Time-of-flight Mass Spectrometry to Detect Breast Cancer Markers in Tears and Serum," Cancer Genomics Proteomics 6(2):75-83 (Mar.-Apr. 2009).
Lee, Han-Byoel, et al. "Development and Validation of a Novel Plasma Protein Signature for Breast Cancer Diagnosis by Using Multiple Reaction Monitoring-based Mass Spectrometry." Anticancer Research 35.11: 6271-6280 (2015).
Li et al., "Proteomics and Bioinformatics Approaches for Identification of Serum Biomarkers to Detect Breast Cancer," Clinical Chemistry 48(8):1296-1304 (2002).
Luftner, D., and Possinger, K., "Nuclear matrix proteins as biomarkers for breast cancer," Expert Rev. Mol. Diagn. 2(1): 23-31 (2002).
Opstal-Van Winden, et al., "Searching for early breast cancer biomarkers by serum protein profiling of pre-diagnostic serum; a nested case-control study." BMC Cancer (2011); 11: 381, 8 pages.
Pieragostino et al., "Unraveling the molecular repertoire of tears as a source of biomarkers: Beyond ocular disease," Proteomics Clin. Appl. 2015, 9, 169-186.
Pisano et al., "Diagnostic Performance of Digital versus Film Mammography for Breast Cancer Screening," The New England Journal of Medicine (2005); 353(17): 1773-1783.
Plavina et al., "Increased Plasma Concentrations of Cytoskeletal and Ca2+Binding Proteins and Their Peptides in Psoriasis Patients," Clinical Chemistry, vol. 54, No. 11, Nov. 1, 2008 (Nov. 1, 2008), pp. 1805-1814.
Reifenstein, "The Treament of Advanced Endometrial Cancer with Hydroxyprogesterone Caproate," Gynecologic Oncology, vol. 2, pp. 377-414 (1974), 38 pages.
Schiess et al., "Targeted proteomic strategy for clinical biomarker discovery," Molecular Oncology 3(1): 33-44 (2009). doi: 10.1016/j.molonc.2008.12.001.
Seth, Arun, et al. "Gene expression profiling of ductal carcinomas in situ and invasive breast tumors." Anticancer Research 23.3A: 2043-2051 (2002).
Storr et al., "Calpain system protein expression in basal-like and triple-negative invasive breast cancer." Annals of Oncology (2012); 23(9): 2289-2296.
Tabár et al., "Swedish Two-County Trial: Impact of Mammographic Screening on Breast Cancer Mortality during 3 Decades," Radiology (2011); 260(3): 658-663.
U.S. Appl. No. 14/707,089, Office Action mailed Apr. 10, 2019, 10 pages.
U.S. Appl. No. 14/707,089, Office Action mailed Aug. 13, 2019, 7 pages.
U.S. Appl. No. 14/707,089, Office Action mailed Feb. 7, 2017, 10 pages.
U.S. Appl. No. 14/707,089, Office Action mailed Mar. 13, 2018, 10 pages.
U.S. Appl. No. 14/707,089, Office Action mailed May 26, 2017, 9 pages.
U.S. Appl. No. 14/707,089, Office Action mailed Oct. 24, 2018, 14 pages.
U.S. Appl. No. 14/707,089, Office Action mailed Sep. 11, 2017, 10 pages.
U.S. Appl. No. 14/879,982, Office Action mailed May 22, 2017, 15 pages.
U.S. Appl. No. 14/879,982, Office Action mailed Nov. 8, 2017, 13 pages.
U.S. Appl. No. 14/879,982, Office Action mailed Oct. 4, 2018, 17 pages.
U.S. Appl. No. 16/356,879, Office Action mailed Nov. 10, 2021, 9 pages.

(56) References Cited

OTHER PUBLICATIONS

Vachon et al., "Mammographic density, breast cancer risk and risk prediction," Breast Cancer Research (2007); 9.6: 217 (2007). (doi:10.1186/bcr1829).

Whelan S.A., et al., "Mass Spectrometry (LC-MS/MS) Identified Proteomic Biosignatures of Breast Cancer in Proximal Fluid," Journal of Proteome Research, Oct. 2012, vol. 11(10), pp. 5034-5045.

Wu, K., and Zhang, Y., "Clinical application of tear proteomics: Present and future prospects," Proteomics Clin. Appl. 1(9):972-982 (2007). (doi:10.1002/prca.200700125).

Xue, et al., "Zinc-α-2-Glycoprotein: A Candidate Biomarker for Colon Cancer Diagnosis in Chinese Population." Int. J. Mol. Sci. (2015), 16(1): 691-703.

Zhang, Lei, et al. "Discovery and preclinical validation of salivary transcriptomic and proteomic biomarkers for the non-invasive detection of breast cancer." PLOS ONE 5.12 : e15573 (2010).

\* cited by examiner

SEQUENCE LISTING

<160> NUMBER OF SEQ ID NOS: 84

<210> SEQ ID NO 1
<211> LENGTH: 10
<212> TYPE: PRT
<213> ORGANISM: Homo sapiens

<400> SEQUENCE: 1

Gln Ser Glu Thr Cys Ser Pro Gly Ser Asp
1               5                   10

<210> SEQ ID NO 2
<211> LENGTH: 8

```
<212> TYPE: PRT
<213> ORGANISM: Homo sapiens

<400> SEQUENCE: 2

Val Thr Met Leu Ile Ser Gly Arg
1               5

<210> SEQ ID NO 3
<211> LENGTH: 11
<212> TYPE: PRT
<213> ORGANISM: Homo sapiens

<400> SEQUENCE: 3

Ala Val Leu Glu Lys Thr Asp Glu Pro Gly Lys
1               5                   10

<210> SEQ ID NO 4
<211> LENGTH: 18
<212> TYPE: PRT
<213> ORGANISM: Homo sapiens

<400> SEQUENCE: 4

Ala Val Leu Glu Lys Thr Asp Glu Pro Gly Lys Tyr Thr Ala Asp Gly
1               5                   10                  15

Gly Lys

<210> SEQ ID NO 5
<211> LENGTH: 13
<212> TYPE: PRT
<213> ORGANISM: Homo sapiens

<400> SEQUENCE: 5

Thr Asp Glu Pro Gly Lys Tyr Thr Ala Asp Gly Gly Lys
1               5                   10

<210> SEQ ID NO 6
<211> LENGTH: 7
<212> TYPE: PRT
<213> ORGANISM: Homo sapiens

<400> SEQUENCE: 6

His Val Ala Tyr Ile Ile Arg
1               5

<210> SEQ ID NO 7
<211> LENGTH: 14
<212> TYPE: PRT
<213> ORGANISM: Homo sapiens

<400> SEQUENCE: 7

Asp Pro Lys Asn Asn Leu Glu Ala Leu Glu Asp Phe Glu Lys
1               5                   10

<210> SEQ ID NO 8
<211> LENGTH: 21
<212> TYPE: PRT
<213> ORGANISM: Homo sapiens

<400> SEQUENCE: 8

Ser His Val Lys Asp His Tyr Ile Phe Tyr Cys Glu Gly Glu Leu His
1               5                   10                  15

Gly Lys Pro Val Arg
            20
```

```
<210> SEQ ID NO 9
<211> LENGTH: 17
<212> TYPE: PRT
<213> ORGANISM: Homo sapiens

<400> SEQUENCE: 9

Asp His Tyr Ile Phe Tyr Cys Glu Gly Glu Leu His Gly Lys Pro Val
1               5                   10                  15

Arg

<210> SEQ ID NO 10
<211> LENGTH: 18
<212> TYPE: PRT
<213> ORGANISM: Homo sapiens

<400> SEQUENCE: 10

Ser His Val Lys Asp His Tyr Ile Phe Tyr Cys Glu Gly Glu Leu His
1               5                   10                  15

Gly Lys

<210> SEQ ID NO 11
<211> LENGTH: 18
<212> TYPE: PRT
<213> ORGANISM: Homo sapiens

<400> SEQUENCE: 11

Leu Val Gly Arg Asp Pro Lys Asn Asn Leu Glu Ala Leu Glu Asp Phe
1               5                   10                  15

Glu Lys

<210> SEQ ID NO 12
<211> LENGTH: 11
<212> TYPE: PRT
<213> ORGANISM: Homo sapiens

<400> SEQUENCE: 12

Gly Leu Ser Thr Glu Ser Ile Leu Ile Pro Arg
1               5                   10

<210> SEQ ID NO 13
<211> LENGTH: 16
<212> TYPE: PRT
<213> ORGANISM: Homo sapiens

<400> SEQUENCE: 13

Asn Asn Leu Glu Ala Leu Glu Asp Phe Glu Lys Ala Ala Gly Ala Arg
1               5                   10                  15

<210> SEQ ID NO 14
<211> LENGTH: 14
<212> TYPE: PRT
<213> ORGANISM: Homo sapiens

<400> SEQUENCE: 14

Tyr Thr Ala Asp Gly Gly Lys His Val Ala Tyr Ile Ile Arg
1               5                   10

<210> SEQ ID NO 15
<211> LENGTH: 16
<212> TYPE: PRT
<213> ORGANISM: Homo sapiens

<400> SEQUENCE: 15
```

Ala Ala Gly Ala Arg Gly Leu Ser Thr Glu Ser Ile Leu Ile Pro Arg
1               5                   10                  15

<210> SEQ ID NO 16
<211> LENGTH: 20
<212> TYPE: PRT
<213> ORGANISM: Homo sapiens

<400> SEQUENCE: 16

Thr Asp Glu Pro Gly Lys Tyr Thr Ala Asp Gly Gly Lys His Val Ala
1               5                   10                  15

Tyr Ile Ile Arg
            20

<210> SEQ ID NO 17
<211> LENGTH: 26
<212> TYPE: PRT
<213> ORGANISM: Homo sapiens

<400> SEQUENCE: 17

Ala Ala Gly Ala Arg Gly Leu Ser Thr Glu Ser Ile Leu Ile Pro Arg
1               5                   10                  15

Gln Ser Glu Thr Cys Ser Pro Gly Ser Asp
            20                  25

<210> SEQ ID NO 18
<211> LENGTH: 14
<212> TYPE: PRT
<213> ORGANISM: Homo sapiens

<400> SEQUENCE: 18

Asp His Tyr Ile Phe Tyr Cys Glu Gly Glu Leu His Gly Lys
1               5                   10

<210> SEQ ID NO 19
<211> LENGTH: 11
<212> TYPE: PRT
<213> ORGANISM: Homo sapiens

<400> SEQUENCE: 19

Asn Asn Leu Glu Ala Leu Glu Asp Phe Glu Lys
1               5                   10

<210> SEQ ID NO 20
<211> LENGTH: 28
<212> TYPE: PRT
<213> ORGANISM: Homo sapiens

<400> SEQUENCE: 20

Ala Met Thr Val Asp Arg Glu Phe Pro Glu Met Asn Leu Glu Ser Val
1               5                   10                  15

Thr Pro Met Thr Leu Thr Thr Leu Glu Gly Gly Asn
            20                  25

<210> SEQ ID NO 21
<211> LENGTH: 21
<212> TYPE: PRT
<213> ORGANISM: Homo sapiens

<400> SEQUENCE: 21

Gly Leu Ser Thr Glu Ser Ile Leu Ile Pro Arg Gln Ser Glu Thr Cys
1               5                   10                  15

-continued

```
Ser Pro Gly Ser Asp
            20

<210> SEQ ID NO 22
<211> LENGTH: 176
<212> TYPE: PRT
<213> ORGANISM: Homo sapiens

<400> SEQUENCE: 22

Met Lys Pro Leu Leu Leu Ala Val Ser Leu Gly Leu Ile Ala Ala Leu
1               5                   10                  15

Gln Ala His His Leu Leu Ala Ser Asp Glu Glu Ile Gln Asp Val Ser
            20                  25                  30

Gly Thr Trp Tyr Leu Lys Ala Met Thr Val Asp Arg Glu Phe Pro Glu
        35                  40                  45

Met Asn Leu Glu Ser Val Thr Pro Met Thr Leu Thr Thr Leu Glu Gly
    50                  55                  60

Gly Asn Leu Glu Ala Lys Val Thr Met Leu Ile Ser Gly Arg Cys Gln
65                  70                  75                  80

Glu Val Lys Ala Val Leu Glu Lys Thr Asp Glu Pro Gly Lys Tyr Thr
                85                  90                  95

Ala Asp Gly Gly Lys His Val Ala Tyr Ile Ile Arg Ser His Val Lys
            100                 105                 110

Asp His Tyr Ile Phe Tyr Cys Glu Gly Glu Leu His Gly Lys Pro Val
        115                 120                 125

Arg Gly Val Lys Leu Val Gly Arg Asp Pro Lys Asn Asn Leu Glu Ala
    130                 135                 140

Leu Glu Asp Phe Glu Lys Ala Ala Gly Ala Arg Gly Leu Ser Thr Glu
145                 150                 155                 160

Ser Ile Leu Ile Pro Arg Gln Ser Glu Thr Cys Ser Pro Gly Ser Asp
                165                 170                 175

<210> SEQ ID NO 23
<211> LENGTH: 10
<212> TYPE: PRT
<213> ORGANISM: Homo sapiens

<400> SEQUENCE: 23

Ala Gly Glu Val Gln Glu Pro Glu Leu Arg
1               5                   10

<210> SEQ ID NO 24
<211> LENGTH: 12
<212> TYPE: PRT
<213> ORGANISM: Homo sapiens

<400> SEQUENCE: 24

Ala Tyr Leu Glu Glu Glu Cys Pro Ala Thr Leu Arg
1               5                   10

<210> SEQ ID NO 25
<211> LENGTH: 10
<212> TYPE: PRT
<213> ORGANISM: Homo sapiens

<400> SEQUENCE: 25

Cys Leu Ala Tyr Asp Phe Tyr Pro Gly Lys
1               5                   10

<210> SEQ ID NO 26
```

```
<211> LENGTH: 16
<212> TYPE: PRT
<213> ORGANISM: Homo sapiens

<400> SEQUENCE: 26

Glu Ile Pro Ala Trp Val Pro Phe Asp Pro Ala Ala Gln Ile Thr Lys
1               5                   10                  15

<210> SEQ ID NO 27
<211> LENGTH: 21
<212> TYPE: PRT
<213> ORGANISM: Homo sapiens

<400> SEQUENCE: 27

His Val Glu Asp Val Pro Ala Phe Gln Ala Leu Gly Ser Leu Asn Asp
1               5                   10                  15

Leu Gln Phe Phe Arg
            20

<210> SEQ ID NO 28
<211> LENGTH: 12
<212> TYPE: PRT
<213> ORGANISM: Homo sapiens

<400> SEQUENCE: 28

Leu Lys Cys Leu Ala Tyr Asp Phe Tyr Pro Gly Lys
1               5                   10

<210> SEQ ID NO 29
<211> LENGTH: 22
<212> TYPE: PRT
<213> ORGANISM: Homo sapiens

<400> SEQUENCE: 29

Asn Ile Leu Asp Arg Gln Asp Pro Pro Ser Val Val Val Thr Ser His
1               5                   10                  15

Gln Ala Pro Gly Glu Lys
            20

<210> SEQ ID NO 30
<211> LENGTH: 17
<212> TYPE: PRT
<213> ORGANISM: Homo sapiens

<400> SEQUENCE: 30

Gln Asp Pro Pro Ser Val Val Val Thr Ser His Gln Ala Pro Gly Glu
1               5                   10                  15

Lys

<210> SEQ ID NO 31
<211> LENGTH: 12
<212> TYPE: PRT
<213> ORGANISM: Homo sapiens

<400> SEQUENCE: 31

Gln Lys Trp Glu Ala Glu Pro Val Tyr Val Gln Arg
1               5                   10

<210> SEQ ID NO 32
<211> LENGTH: 10
<212> TYPE: PRT
<213> ORGANISM: Homo sapiens

<400> SEQUENCE: 32
```

Trp Glu Ala Glu Pro Val Tyr Val Gln Arg
1               5                   10

<210> SEQ ID NO 33
<211> LENGTH: 25
<212> TYPE: PRT
<213> ORGANISM: Homo sapiens

<400> SEQUENCE: 33

Tyr Ser Lys Asn Ile Leu Asp Arg Gln Asp Pro Ser Val Val Val
1               5                   10                  15

Thr Ser His Gln Ala Pro Gly Glu Lys
            20                  25

<210> SEQ ID NO 34
<211> LENGTH: 12
<212> TYPE: PRT
<213> ORGANISM: Homo sapiens

<400> SEQUENCE: 34

Tyr Ser Leu Thr Tyr Ile Tyr Thr Gly Leu Ser Lys
1               5                   10

<210> SEQ ID NO 35
<211> LENGTH: 13
<212> TYPE: PRT
<213> ORGANISM: Homo sapiens

<400> SEQUENCE: 35

Tyr Tyr Tyr Asp Gly Lys Asp Tyr Ile Glu Phe Asn Lys
1               5                   10

<210> SEQ ID NO 36
<211> LENGTH: 13
<212> TYPE: PRT
<213> ORGANISM: Homo sapiens

<400> SEQUENCE: 36

Ala Tyr Leu Glu Glu Glu Cys Pro Ala Thr Leu Arg Lys
1               5                   10

<210> SEQ ID NO 37
<211> LENGTH: 15
<212> TYPE: PRT
<213> ORGANISM: Homo sapiens

<400> SEQUENCE: 37

Ala Lys Ala Tyr Leu Glu Glu Glu Cys Pro Ala Thr Leu Arg Lys
1               5                   10                  15

<210> SEQ ID NO 38
<211> LENGTH: 16
<212> TYPE: PRT
<213> ORGANISM: Homo sapiens

<400> SEQUENCE: 38

Gln Val Glu Gly Met Glu Asp Trp Lys Gln Asp Ser Gln Leu Gln Lys
1               5                   10                  15

<210> SEQ ID NO 39
<211> LENGTH: 17
<212> TYPE: PRT
<213> ORGANISM: Homo sapiens

<400> SEQUENCE: 39

Cys Leu Ala Tyr Asp Phe Tyr Pro Gly Lys Ile Asp Val His Trp Thr
1               5                   10                  15

Arg

<210> SEQ ID NO 40
<211> LENGTH: 297
<212> TYPE: PRT
<213> ORGANISM: Homo sapiens

<400> SEQUENCE: 40

Met Val Arg Met Val Pro Val Leu Leu Ser Leu Leu Leu Leu Leu Gly
1               5                   10                  15

Pro Ala Val Pro Gln Glu Asn Gln Asp Gly Arg Tyr Ser Leu Thr Tyr
                20                  25                  30

Ile Tyr Thr Gly Leu Ser Lys His Val Glu Asp Val Pro Ala Phe Gln
            35                  40                  45

Ala Leu Gly Ser Leu Asn Asp Leu Gln Phe Phe Arg Tyr Asn Ser Lys
        50                  55                  60

Asp Arg Lys Ser Gln Pro Met Gly Leu Trp Arg Gln Val Glu Gly Met
65                  70                  75                  80

Glu Asp Trp Lys Gln Asp Ser Gln Leu Gln Lys Ala Arg Glu Asp Ile
                85                  90                  95

Phe Met Glu Thr Leu Lys Asp Ile Val Glu Tyr Tyr Asn Asp Ser Asn
            100                 105                 110

Gly Ser His Val Leu Gln Gly Arg Phe Gly Cys Glu Ile Glu Asn Asn
        115                 120                 125

Arg Ser Ser Gly Ala Phe Trp Lys Tyr Tyr Tyr Asp Gly Lys Asp Tyr
130                 135                 140

Ile Glu Phe Asn Lys Glu Ile Pro Ala Trp Val Pro Phe Asp Pro Ala
145                 150                 155                 160

Ala Gln Ile Thr Lys Gln Lys Trp Glu Ala Glu Pro Val Tyr Val Gln
                165                 170                 175

Arg Ala Lys Ala Tyr Leu Lys Glu Glu Cys Pro Ala Thr Leu Arg Leu
            180                 185                 190

Tyr Leu Lys Tyr Ser Lys Asn Ile Leu Asp Arg Gln Asp Pro Pro Ser
        195                 200                 205

Val Val Val Thr Ser His Gln Ala Pro Gly Glu Lys Lys Leu Lys
210                 215                 220

Cys Leu Ala Tyr Asp Phe Tyr Pro Gly Lys Ile Asp Val His Trp Thr
225                 230                 235                 240

Arg Ala Gly Glu Val Gln Glu Pro Glu Leu Arg Gly Asp Val Leu His
                245                 250                 255

Asn Gly Asn Gly Thr Tyr Gln Ser Trp Val Val Ala Val Pro Pro Gln
            260                 265                 270

Asp Thr Ala Pro Tyr Ser Cys His Val Gln His Ser Ser Leu Ala Gln
        275                 280                 285

Pro Leu Val Val Pro Trp Glu Ala Ser
    290                 295

<210> SEQ ID NO 41
<211> LENGTH: 120
<212> TYPE: PRT
<213> ORGANISM: Homo sapiens

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asn Met Asn Trp Val Arg Gln Val Thr Gly Lys Gly Leu Glu Trp Val
            35                  40                  45

Ser Ala Ile Gly Thr Ala Gly Asp Gln Tyr Tyr Ala Asp Ser Val Lys
    50                  55                  60

Gly Arg Phe Thr Ile Ser Arg Asn Asp Ser Lys Asn Thr Leu Tyr Leu
65                  70                  75                  80

Asn Met Asn Ser Leu Arg Ala Glu Asp Thr Ala Val Tyr Tyr Cys Ala
                85                  90                  95

Arg Ser Pro Val Ser Leu Val Asp Gly Trp Leu Tyr Tyr Tyr Tyr Gly
            100                 105                 110

Ser Val Trp Gly Gln Gly Thr Leu
        115                 120
```

<210> SEQ ID NO 42
<211> LENGTH: 19
<212> TYPE: PRT
<213> ORGANISM: Homo sapiens

<400> SEQUENCE: 42

```
Glu Val Gln Leu Val Glu Ser Gly Gly Gly Leu Val Gln Pro Gly Gly
1               5                   10                  15

Ser Leu Arg
```

<210> SEQ ID NO 43
<211> LENGTH: 11
<212> TYPE: PRT
<213> ORGANISM: Homo sapiens

<400> SEQUENCE: 43

```
Ala Glu Asp Thr Ala Val Tyr Tyr Cys Ala Arg
1               5                   10
```

<210> SEQ ID NO 44
<211> LENGTH: 119
<212> TYPE: PRT
<213> ORGANISM: Homo sapiens

<400> SEQUENCE: 44

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
```

```
                115

<210> SEQ ID NO 45
<211> LENGTH: 13
<212> TYPE: PRT
<213> ORGANISM: Homo sapiens

<400> SEQUENCE: 45

Ile Gln Val Tyr Ser Arg His Pro Ala Glu Asn Gly Lys
1               5                   10

<210> SEQ ID NO 46
<211> LENGTH: 22
<212> TYPE: PRT
<213> ORGANISM: Homo sapiens

<400> SEQUENCE: 46

Ser Asn Phe Leu Asn Cys Tyr Val Ser Gly Phe His Pro Ser Asp Ile
1               5                   10                  15

Glu Val Asp Leu Leu Lys
            20

<210> SEQ ID NO 47
<211> LENGTH: 13
<212> TYPE: PRT
<213> ORGANISM: Homo sapiens

<400> SEQUENCE: 47

Ile Glu Lys Val Glu His Ser Asp Leu Ser Phe Ser Lys
1               5                   10

<210> SEQ ID NO 48
<211> LENGTH: 10
<212> TYPE: PRT
<213> ORGANISM: Homo sapiens

<400> SEQUENCE: 48

Val Glu His Ser Asp Leu Ser Phe Ser Lys
1               5                   10

<210> SEQ ID NO 49
<211> LENGTH: 10
<212> TYPE: PRT
<213> ORGANISM: Homo sapiens

<400> SEQUENCE: 49

Val Asn His Val Thr Leu Ser Gln Pro Lys
1               5                   10

<210> SEQ ID NO 50
<211> LENGTH: 16
<212> TYPE: PRT
<213> ORGANISM: Homo sapiens

<400> SEQUENCE: 50

Asp Glu Tyr Ala Cys Arg Val Asn His Val Thr Leu Ser Gln Pro Lys
1               5                   10                  15

<210> SEQ ID NO 51
<211> LENGTH: 132
<212> TYPE: PRT
<213> ORGANISM: Homo sapiens

<400> SEQUENCE: 51
```

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
            85                  90                  95

Leu Met Leu Asn Pro Pro Asn Phe Cys Glu Met Asp Gly Gln Cys Lys
        100                 105                 110

Arg Asp Leu Lys Cys Cys Met Gly Met Cys Gly Lys Ser Cys Val Ser
            115                 120                 125

Pro Val Lys Ala
    130

<210> SEQ ID NO 52
<211> LENGTH: 14
<212> TYPE: PRT
<213> ORGANISM: Homo sapiens

<400> SEQUENCE: 52

Ala Gly Val Cys Pro Pro Lys Lys Ser Ala Gln Cys Leu Arg
1               5                   10

<210> SEQ ID NO 53
<211> LENGTH: 21
<212> TYPE: PRT
<213> ORGANISM: Homo sapiens

<400> SEQUENCE: 53

Cys Cys Pro Asp Thr Cys Gly Ile Lys Cys Leu Asp Pro Val Asp Thr
1               5                   10                  15

Pro Asn Pro Thr Arg
            20

<210> SEQ ID NO 54
<211> LENGTH: 12
<212> TYPE: PRT
<213> ORGANISM: Homo sapiens

<400> SEQUENCE: 54

Cys Leu Asp Pro Val Asp Thr Pro Asn Pro Thr Arg
1               5                   10

<210> SEQ ID NO 55
<211> LENGTH: 15
<212> TYPE: PRT
<213> ORGANISM: Homo sapiens

<400> SEQUENCE: 55

Tyr Lys Lys Pro Glu Cys Gln Ser Asp Trp Gln Cys Pro Gly Lys
1               5                   10                  15

<210> SEQ ID NO 56
<211> LENGTH: 8
<212> TYPE: PRT
<213> ORGANISM: Homo sapiens

<400> SEQUENCE: 56

Ser Cys Val Ser Pro Val Lys Ala
1               5

<210> SEQ ID NO 57
<211> LENGTH: 13
<212> TYPE: PRT
<213> ORGANISM: Homo sapiens

<400> SEQUENCE: 57

Lys Pro Glu Cys Gln Ser Asp Trp Gln Cys Pro Gly Lys
1               5                   10

<210> SEQ ID NO 58
<211> LENGTH: 19
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15

Ser Leu Arg

<210> SEQ ID NO 59
<211> LENGTH: 10
<212> TYPE: PRT
<213> ORGANISM: Homo sapiens

<400> SEQUENCE: 59

Glu Asp Thr Ala Val Tyr Tyr Cys Ala Lys
1               5                   10

<210> SEQ ID NO 60
<211> LENGTH: 117
<212> TYPE: PRT
<213> ORGANISM: Homo sapiens

<400> SEQUENCE: 60

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Ala Met Ser Trp Val Arg Gln Ala Phe Gly Lys Gly Leu
        50                  55                  60

Glu Trp Val Ser Ala Ile Ser Gly Ser Gly Gly Ser Thr Tyr Tyr Gly
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Ala Lys
            115

<210> SEQ ID NO 61
<211> LENGTH: 15
<212> TYPE: PRT
<213> ORGANISM: Homo sapiens -continued

<400> SEQUENCE: 61

Ala Val Ser Phe Ser Gln Val Val Ala Gly Thr Asn Phe Ile Lys
1               5                   10                  15

<210> SEQ ID NO 62
<211> LENGTH: 12
<212> TYPE: PRT
<213> ORGANISM: Homo sapiens

<400> SEQUENCE: 62

Ser Gln Val Val Ala Gly Thr Asn Tyr Phe Ile Lys
1               5                   10

<210> SEQ ID NO 63
<211> LENGTH: 22
<212> TYPE: PRT
<213> ORGANISM: Homo sapiens

<400> SEQUENCE: 63

Val Phe Gln Ser Leu Pro His Glu Asn Lys Pro Leu Glu Thr Leu Ser
1               5                   10                  15

Asn Tyr Gln Thr Asn Lys
            20

<210> SEQ ID NO 64
<211> LENGTH: 12
<212> TYPE: PRT
<213> ORGANISM: Homo sapiens

<400> SEQUENCE: 64

Val His Val Gly Asp Glu Asp Phe Val His Leu Arg
1               5                   10

<210> SEQ ID NO 65
<211> LENGTH: 98
<212> TYPE: PRT
<213> ORGANISM: Homo sapiens

<400> SEQUENCE: 65

Met Met Cys Gly Ala Pro Ser Ala Thr Gln Pro Ala Thr Ala Glu Thr
1               5                   10                  15

Gln His Ile Ala Asp Gln Val Arg Ser Gln Leu Glu Glu Lys Glu Asn
            20                  25                  30

Lys Lys Phe Pro Val Phe Lys Ala Val Ser Phe Lys Ser Gln Val Val
        35                  40                  45

Ala Gly Thr Asn Tyr Phe Ile Lys Val His Val Gly Asp Glu Asp Phe
    50                  55                  60

Val His Leu Arg Val Phe Gln Ser Leu Pro His Glu Asn Lys Pro Leu
65                  70                  75                  80

Thr Leu Ser Asn Tyr Gln Thr Asn Lys Ala Lys His Asp Glu Leu Thr
                85                  90                  95

Tyr Phe

<210> SEQ ID NO 66
<211> LENGTH: 19
<212> TYPE: PRT
<213> ORGANISM: Homo sapiens

<400> SEQUENCE: 66

Ser Tyr Glu Leu Thr Gln Pro Pro Ser Val Ser Val Ser Pro Gly Gln
1               5                   10                  15

Thr Ala Arg

<210> SEQ ID NO 67
<211> LENGTH: 11
<212> TYPE: PRT
<213> ORGANISM: Homo sapiens

<400> SEQUENCE: 67

Ile Gln Val Leu Val Glu Pro Asp His Phe Lys
1               5                   10

<210> SEQ ID NO 68
<211> LENGTH: 13
<212> TYPE: PRT
<213> ORGANISM: Homo sapiens

<400> SEQUENCE: 68

Gln Ser Val Phe Pro Phe Glu Ser Gly Lys Pro Phe Lys
1               5                   10

<210> SEQ ID NO 69
<211> LENGTH: 14
<212> TYPE: PRT
<213> ORGANISM: Homo sapiens

<400> SEQUENCE: 69

Val Ile Val Cys Asn Thr Lys Leu Asp Asn Asn Trp Gly Arg
1               5                   10

<210> SEQ ID NO 70
<211> LENGTH: 7
<212> TYPE: PRT
<213> ORGANISM: Homo sapiens

<400> SEQUENCE: 70

Ile Ala Leu Asp Phe Gln Arg
1               5

<210> SEQ ID NO 71
<211> LENGTH: 14
<212> TYPE: PRT
<213> ORGANISM: Homo sapiens

<400> SEQUENCE: 71

Val Ala Val Asn Asp Ala His Leu Leu Gln Tyr Asn His Arg
1               5                   10

<210> SEQ ID NO 72
<211> LENGTH: 11
<212> TYPE: PRT
<213> ORGANISM: Homo sapiens

<400> SEQUENCE: 72

Gly Asn Asp Val Ala Phe His Phe Asn Pro Arg
1               5                   10

<210> SEQ ID NO 73
<211> LENGTH: 15
<212> TYPE: PRT
<213> ORGANISM: Homo sapiens

<400> SEQUENCE: 73

Met Leu Ile Thr Ile Leu Gly Thr Val Lys Pro Asn Ala Asn Arg
1               5                   10                  15

<210> SEQ ID NO 74
<211> LENGTH: 15
<212> TYPE: PRT
<213> ORGANISM: Homo sapiens

<400> SEQUENCE: 74

Arg Val Ile Val Cys Asn Thr Lys Leu Asp Asn Asn Trp Gly Arg
1               5                   10                  15

<210> SEQ ID NO 75
<211> LENGTH: 7
<212> TYPE: PRT
<213> ORGANISM: Homo sapiens

<400> SEQUENCE: 75

Lys Leu Asn Glu Ile Ser Lys
1               5

<210> SEQ ID NO 76
<211> LENGTH: 107
<212> TYPE: PRT
<213> ORGANISM: Homo sapiens

<400> SEQUENCE: 76

Ser Tyr Glu Leu Thr Gln Pro Pro Ser Val Ser Val Ser Pro Gly Gln
1               5                   10                  15

Thr Ala Arg Ile Thr Cys Ser Ala Asn Ala Leu Pro Asn Gln Tyr Ala
            20                  25                  30

Tyr Trp Tyr Gln Gln Lys Pro Gly Arg Ala Pro Val Met Val Ile Tyr
        35                  40                  45

Lys Asp Thr Gln Arg Pro Ser Gly Ile Pro Gln Arg Phe Ser Ser Ser
    50                  55                  60

Thr Ser Gly Thr Thr Val Thr Leu Thr Ile Ser Gly Val Gln Ala Glu
65                  70                  75                  80

Asp Glu Ala Asp Tyr Tyr Cys Gln Ala Trp Asp Asn Ser Ala Ser Ile
                85                  90                  95

Phe Gly Gly Gly Thr Lys Leu Thr Val Leu Gly
            100                 105

<210> SEQ ID NO 77
<211> LENGTH: 250
<212> TYPE: PRT
<213> ORGANISM: Homo sapiens

<400> SEQUENCE: 77

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly

```
            100                 105                 110
Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
            210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 78
<211> LENGTH: 146
<212> TYPE: PRT
<213> ORGANISM: Homo sapiens

<400> SEQUENCE: 78

Met Ala Gly Glu Leu Thr Pro Glu Glu Ala Gln Tyr Lys Lys Ala
1               5                   10                  15

Phe Ser Ala Val Asp Thr Asp Gly Asn Gly Thr Ile Asn Ala Gln Glu
                20                  25                  30

Leu Gly Ala Ala Leu Lys Ala Thr Gly Lys Asn Leu Ser Glu Ala Gln
            35                  40                  45

Leu Arg Lys Leu Ile Ser Glu Val Asp Ser Asp Gly Asp Gly Glu Ile
        50                  55                  60

Ser Phe Gln Glu Phe Leu Thr Ala Ala Lys Lys Ala Arg Ala Gly Leu
65                  70                  75                  80

Glu Asp Leu Gln Val Ala Phe Arg Ala Phe Asp Gln Asp Gly Asp Gly
                85                  90                  95

His Ile Thr Val Asp Glu Leu Arg Arg Ala Met Ala Gly Leu Gly Gln
            100                 105                 110

Pro Leu Pro Gln Glu Glu Leu Asp Ala Met Ile Arg Glu Ala Asp Val
        115                 120                 125

Asp Gln Asp Gly Arg Val Asn Tyr Glu Glu Phe Ala Arg Met Leu Ala
    130                 135                 140

Gln Glu
145

<210> SEQ ID NO 79
<211> LENGTH: 14
<212> TYPE: PRT
<213> ORGANISM: Homo sapiens

<400> SEQUENCE: 79

Ala Gly Glu Leu Thr Pro Glu Glu Ala Gln Tyr Lys Lys
1               5                   10
```

```
<210> SEQ ID NO 80
<211> LENGTH: 24
<212> TYPE: PRT
<213> ORGANISM: Homo sapiens

<400> SEQUENCE: 80

Lys Ala Phe Ser Ala Val Asp Thr Asp Gly Asn Gly Thr Ile Asn Ala
1               5                   10                  15

Gln Glu Leu Gly Ala Ala Leu Lys
            20

<210> SEQ ID NO 81
<211> LENGTH: 23
<212> TYPE: PRT
<213> ORGANISM: Homo sapiens

<400> SEQUENCE: 81

Ala Phe Ser Ala Val Asp Thr Asp Gly Asn Gly Thr Ile Asn Ala Gln
1               5                   10                  15

Glu Leu Gly Ala Ala Leu Lys
            20

<210> SEQ ID NO 82
<211> LENGTH: 11
<212> TYPE: PRT
<213> ORGANISM: Homo sapiens

<400> SEQUENCE: 82

Ala Gly Leu Glu Asp Leu Gln Val Ala Phe Arg
1               5                   10

<210> SEQ ID NO 83
<211> LENGTH: 17
<212> TYPE: PRT
<213> ORGANISM: Homo sapiens

<400> SEQUENCE: 83

Glu Ala Asp Val Asp Gln Asp Gly Arg Val Asn Tyr Glu Glu Phe Ala
1               5                   10                  15

Arg

<210> SEQ ID NO 84
<211> LENGTH: 8
<212> TYPE: PRT
<213> ORGANISM: Homo sapiens

<400> SEQUENCE: 84

Asn Leu Ser Glu Ala Gln Leu Arg
1               5
```

METHODS OF DETECTING CANCER

CROSS REFERENCE TO RELATED APPLICATIONS

This application is a continuation of U.S. patent application Ser. No. 16/356,879, filed Mar. 18, 2019, which is a continuation of U.S. patent application Ser. No. 14/879,982, filed Oct. 9, 2015, which claims the benefit of U.S. Provisional Patent Application No. 62/061,900, filed on Oct. 9, 2014, and which is a continuation-in-part of U.S. patent application Ser. No. 14/707,089, filed May 8, 2015, entitled "Methods of Cancer," which claims priority to U.S. Provisional Application No. 61/991,061 filed on May 9, 2014. The disclosures of each of the above-referenced applications are herein incorporated by reference in their entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is NAMI_001_05US_ST25.txt. The text file is about 29,045 bytes, was created on Apr. 24, 2025, and is being submitted electronically via USPTO Patent Center.

BACKGROUND

The present application encompasses proteins and peptide fragments of those proteins, which are produced by proteolytic digestion of the proteins, and which both proteins and peptide fragments are useful for diagnosing of cancer or for monitoring for the presence of cancer in an individual.

Screening mammograms typically have a sensitivity of 75% and specificity of around 98% resulting in a false positive rate of roughly 5% per mammogram (Brown, Houn, Sickles, & Kessler, 1995; Kolb, Lichy, & Newhouse, 2002; Luftner & Possinger, 2002). Breast tissue type, more specifically density, also greatly influences the performance of mammography. The degree of breast density is classified using the American College of Radiology Breast Imaging Reporting and Data System (BI-RADS). This system consists of four classifications 1-4; where category 1 is mostly fatty (<25% dense); category 2 is scattered fibroglandular densities (25-50% dense); category 3 is heterogeneously dense (51-75% dense) and category 4 is extremely dense (>75% dense) (Bigenwald, 2008; Klifa, 2010; Scheel, 2014).

For women with fatty breast tissue, mammography can be an effective screening tool, when patients are compliant with yearly screenings (Tabar, 2001; Pisano, 2005). However, as breast density increases, the effectiveness of mammography decreases leading to increased follow up imaging and, more importantly, missed cancer diagnosis. Mammographic sensitivity, for high-risk patients, has been shown to be as low as 31% for category 1, 27% for category 2, 20% for category 3, and 12.5% for category 4 (Bigenwald, 2008). Approximately fifty percent of the female population is in categories 3 and 4, which is considered dense breast tissue (Vachon, 2007). Currently, the best screening option for these women is MRI, which can be up to 10 times more expensive than mammography (Beignwald, 2008). Lack of good screening options is a serious problem as women with 75% or more dense tissue have four to six times greater risk of developing breast cancer than women with less dense tissue (Boyd, 2007).

Follow up imaging to evaluate false positives costs the US over 4 billion dollars with an additional 1.6 billion dollars spent for biopsies alone. In 2010 of the 1.6 million biopsies performed, as few as 16% (only 261,000) were found to have cancer (Grady, 2012). The answer to increasing the diagnostic parameters of imaging can be found in the pre- and post-image diagnostics that focus on genetic and proteomic information, more specifically, biomarkers (Armstrong, Handed, Chen, & Bristol Demeter, 2013; Li, Zhang, Rosenzweig, Wang, & Chan, 2002).

Tissue and serum are commonly the most logical place for beginning biomarker research, however the large dynamic range of both mediums makes discovery quite difficult (Schiess, Wollscheid, & Aebersold, 2009). The answers may lie in less complex biological fluids, such as saliva and tears. The use of tears as diagnostic medium is not a novel application as the tear proteome has been extensively investigated previously (Bohm et al., 2012; 2011; Lebrecht, Boehm, Schmidt, Koelbl, & Grus, 2009a; Lebrecht et al., 2009b; Wu & Zhang, 2007). In this application a quantitative assay for the detection of a panel of tear-based biomarkers in response to cancer is disclosed. From this quantitative information, the framework for a Certified Laboratory Improvement Amendments (CLIA) protocol will be defined.

SUMMARY

Methods of determining whether a subject has cancer are provided herein. Methods include obtaining a sample from the subject and performing steps of detecting the level of at least one of the markers selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTE), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IdHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn] (SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADHIG), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-(PROF1), Cluster of Ig lambda chain V-III region LOT (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (IT1H2), Mucin-like protein 1 (MUCL1), S100 A6 (S100A6), Na(+)/H(+) exchange regulatory cofactor NHE-RF1 (NHRE1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (EBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-48 chain (TBB4B), Tropomyosin alpha-3 chain (TPM3), Serotransferrin (TREE), Glutathione S-transferase P (THIO), Vitronectin (VTNC), Vitamin D Binding protein (Q6LDC6), Inter-alpha-trypsin inhibitor heavy chain H4 (ITIFI4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY). The subject is likely to have cancer if the levels of these markers change in comparison to the levels in a control sample from a subject lacking cancer. The sample is optimally an ocular sample, such as an isolated tear sample or ocular wash, but can also be from saliva, or other bodily fluid. An ocular sample indicates a tear sample encompassing secretions from the lacrimal gland and other tissues that connect with the lymphatic system.

Kits for performing methods described herein are also provided. Kits can contain a sample collection platform, a tube for collection and extraction that can comprise a protease inhibitor or other protein-stabilizing agent, sample extraction reagents and testing apparatus.

DETAILED DESCRIPTION

Figure 1:
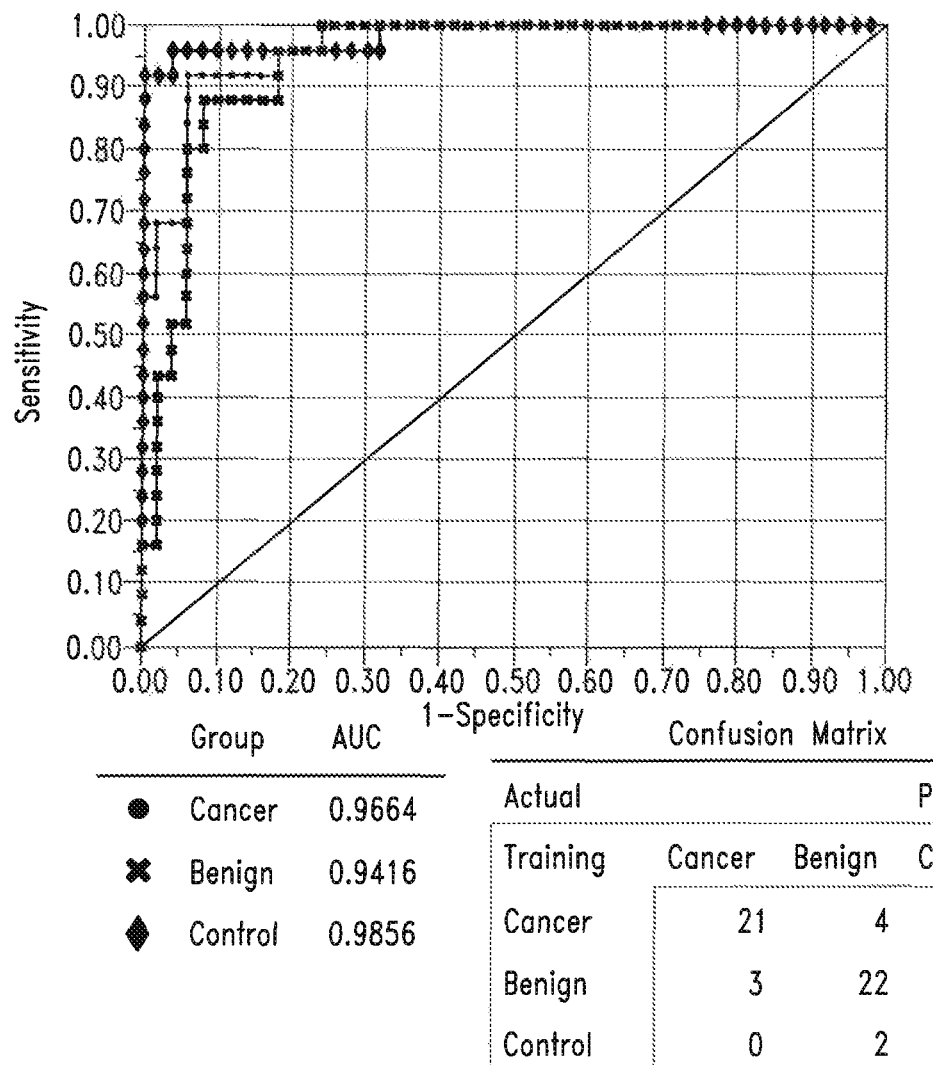
FIG. 1: ANOVA of spectral intensities for the following proteins identified in Experiment 1: (A) Ig Heavy Chain V-IV region HiL, (B) Ig Heavy Chain region V-III region BRO, (C) Ig Heavy Chain V-III region VH26, (D) Antileukoproteinase, (E) β2 Microglobulin, (F) Calmodulin like protein 5, (G) Lipocalin 1, (H) Cystatin B, (I) Galectin 3, (J) Zinc-α 2 glycoprotein.

Provided herein are proteins and peptide fragments obtained by trypsin digestion from ocular samples. The produced polypeptides are selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S100A9), S100A8 (S10A5), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn] (SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (ASMU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-1 (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain R2 (IT1H2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-1 region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (IT1H4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY). The trypsin sequences and full-length amino acid sequences of the proteins identified as being down regulated in cancer samples are provided in Appendix 1.

The protein and peptides are shown in the Examples to either increase or decrease in biological samples in response to the presence of breast cancer as compared to controls. These proteins and peptides are biomarkers and will be used to determine the disease state of a patient or other subject.

Subjects include humans, domesticated animals such as cats, dogs, cows, pigs, or other animals susceptible to cancer. A "patient" indicates a subject who is diagnosed with a disease, or with cancer, or is being tested for having cancer. Thus the terms subject and patient can be used interchangeably herein. The subjects can be suspected of having cancer. The subject can be suspected of having cancer, including breast cancer, acoustic neuroma, acute lymphoblastic leukemia, acute myelogenous leukemia, adrenal tumors, AIDS-associated cancers, basal cell carcinoma, benign blood disorders, bladder cancer, bone cancer, brain tumors (metastatic and primary), breast cancer, cancer of unknown primary origin, cervical cancer, chronic lymphocytic leukemia, chronic myelogenous leukemia, colorectal cancer, esophageal cancer, gallbladder and bile duct cancers, gastrointestinal neuroendocrine tumors, GERD, Barrett's esophagus and achalasia, gestational trophoblastic disease, head and neck cancers, Kaposi sarcoma, kidney cancer, leukemias, liver cancer, liver metastases, low-grade glioma, lung cancer, lymphoma, male breast cancer, melanoma, Merkel cell carcinoma, mesothelioma, multiple myeloma, myelodysplastic syndrome, ovarian cancer, pancreatic cancer, pancreatic cysts, pituitary tumors, prostate cancer, pulmonary neuroendocrine tumors, rare blood disorder, skin cancer, soft tissue sarcoma, spine tumors, squamous cell carcinoma, stomach (gastric) cancer, testicular cancer (germ cell tumors), thymoma and other thymic tumors, tracheal diseases, uterine (endometrial) cancer, uterine sarcoma. The subjects can have an increased risk of developing breast cancer. For example, the subject can be at increased risk of cancer, or suspected of having cancer because of a positive mammography result, by detection of a lump in the breast, testing positive for a gene known to increase the risk of cancer such as BRCA, or already had a resection, biopsy, or other procedure to remove the cancer. The subject can be undergoing, or have previously undergone, treatment for cancer and methods and kits herein are used to monitor progression of treatment or alternatively to monitor for recurrence or spread of the cancer.

Also provided herein are methods and kits to collect ocular samples for use in determining the expression levels of the identified proteins or polypeptides in lacrimal secretions. The use of collection strips and tubes containing protease inhibitor or protein stabilizing agents is disclosed. Kits further contain buffers or reagents for the elution of breast cancer biomarkers from the collection strips that have been in contact with an eye to collect lacrimal secretions. The design of devices to collect proteins from the ocular cavity, as well as the packaging of this device with a container to house the collection device and elution buffers, is disclosed.

Methods disclosed herein encompass the use of these cancer biomarkers, singly or in multiples, in a CLIA based protocol utilizing a triple quadrupole LC-MS/MS platform, which will be carried out at a centralized laboratory testing facility. The ocular samples collected from individuals can be shipped to the testing facility in this embodiment. The identified proteins and their subsequent proteolytic fragments, as shown in Appendix I, are used for quantitative analysis of diagnostic peptides produced in the triple quad. A threshold value or a relative or actual value in terms of polypeptide concentration directly relating to the polypeptides selected from the following and as listed in Table 1: Ig lambda chain V-IV region Hi1 (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn] (SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodulin-like protein 5 (CALL5), Alpha-1-antitrypsin (A1AT), Alpha-1B-glycoprotein (A1BG). Leucine-rich alpha-2-glycoprotein (A2GL). Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-1 (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (IT1H2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (R1NI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), ComplementC3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) can be defined or samples can be compared directly to non-cancerous controls. The quantitative information in report form can be provided to physicians to help in making decisions regarding the pathway of patient care. Physicians can base treatment decisions on these results and the final step can include administration of an appropriate anti-cancer therapeutic to the subject.

In an alternate embodiment, the polypeptides selected from the following and as listed in Table 1: Ig lambda chain V-IV region Hi1 (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn] (SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1, (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-1 (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (IT1H2), Mucin-like protein 1 (MUCL1), S100A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-1 region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (CORIA), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14.3-3 sigma (1433S), alpha-2-hs-glycoprotein (FETUA), alpha-2-macroglobulin (A2MG), Transthyretin (TTHY) can be detected by implementing binding agents, for example antibodies, peptoids, or coated surfaces, and reagents that accommodate a binding interaction specific to these proteins to produce a reaction that can be quantitated based on production of a detectable signal such as florescence, color change, or UV absorbance. Implementing these components in a cartridge with a partnering reading instrument, such as a point-of-care device that can be used at point of care is also provided. Binding agents for these proteins and polypeptides can also be used for detection in a lateral flow device. Thus, methods of detecting the level of protein expression in the samples using a binding partner such as an antibody can be used to detect the markers provided herein in an immunoassay.

The immunoassay typically includes contacting a test sample with an antibody or antigen that specifically binds to, or otherwise recognizes a biomarker, and detecting the presence of a complex of the antibody or antigen bound to the biomarker in the sample. The immunoassay procedure can be selected from a wide variety of immunoassay procedures known in the art involving recognition of antibody/antigen complexes, including enzyme-linked immunosorbent assays (ELISA), radioimmunoassay (RIA), and Western blots, and use of multiplex assays, including use of antibody arrays, wherein several desired antibodies are placed on a support, such as a glass bead or plate, and reacted or otherwise contacted with the test sample. Such assays are well-known to the skilled artisan.

The detection of the biomarkers described herein in a sample can be performed in a variety of ways. In one embodiment, the method provides the reverse-transcription of complementary DNAs from mRNAs obtained from the sample. Fluorescent dye-labeled complementary RNAs can be transcribed from complementary DNAs that are then hybridized to the arrays of oligonucleotide probes. The fluorescent color generated by hybridization can be read by machine, such as a SureScan microarray scanner (Agilent Technologies) and data obtained and processed using software, such as Agilent Feature Extraction Software (9.1). Such array-based methods include microarray analysis to develop a gene expression profile. As used herein, the term "gene expression profile" refers to the expression levels of mRNAs or proteins of a panel of genes in the subject. As used herein, the term "diagnostic panel" refers to a panel of genes, peptides or proteins with an expression level that can be relied on to diagnose or predict the status of the disease. Included in this panel are genes, peptides and proteins selected from the following and as listed in Table 1: Ig lambda chain V-IV region Hi1 (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3). Histidine triad nucleotide-binding protein 1 (D6RD60), S10A9 (S10A9), S100A8 (S10A8), Galectin-3-binding protein (LG3BP), Cluster of Ig alpha-1 chain C region (IGHA1), Cluster of Ig kappa chain V-II region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn] (SODC), SPARC-like protein 1 (SPRL1), Ig heavy chain V-III region TIL (HV304), Keratin (K1C9), Cystatin-SN (CYTN). Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-1 (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7V574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (C03), Coronin-1A (COR1A), Programmed cell death 6-interacting protein (DCD), Defensin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) as well as any combination thereof, as provided herein.

In other embodiments, complementary DNAs are reverse-transcribed from mRNAs obtained from the sample, amplified, and simultaneously quantified by real-time PCR, thereby enabling both detection and quantification (as absolute number of copies or relative amount when normalized to DNA input or additional normalizing genes) of a specific gene product in the complementary DNA sample as well as the original mRNA sample.

The methods of the versions of this invention include detecting at least one biomarker. However, any number of biomarkers can be detected. It is preferred that at least two biomarkers are detected in the analysis. However, it is realized that three, four, or more, including all, of the biomarkers described herein can be utilized in the analysis. Thus, not only can one or more markers be detected, any number or combination of markers can be used in detection. In addition, other biomarkers not herein described can be combined with any of the presently disclosed biomarkers to aid in the diagnosis of cancer. Moreover, any combination of the above biomarkers can be detected in accordance with versions of the present invention.

The markers selected from the following and as listed in Table 1: Ig lambda chain V-1V region Hi1 (LV403), Ig heavy chain V-III BRO(HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn]

(SODC), SPARC-like protein 1 (SPRL1), Ig heavy chain V-III region TIL (HV304), Keratin (KIC9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C93V77), Caireticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase (Mn), mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) can increase or decrease at least 1.5 fold, 2 fold, 4 fold, 5 fold, 8 fold, 10 fold or more, relative to the level of the marker in the control sample. The control sample can be a sample from a subject that does not have cancer, a pooled sample from subjects that do not have cancer, or can be a control or baseline expression level known to be the average expression level of subjects without cancer.

Several terms are used throughout this disclosure and should be defined as commonly used in the art, or as specifically provided herein. As provided herein, mass spectrometry or MS refers to an analytical technique generating electrical or magnetic fields to determine mass-to-charge ratio of peptides and chemical compounds in order to identify or determine peptide sequence and chemical structures. LC-MS/MS spectrometry refers to an analytical technique combining the separation capabilities of high performance liquid chromatography (HPLC) with the mass analysis of mass spectrometry. Triple quadrupole mass spectrometry refers to a tandem mass spectrometer with three ionizing chambers (Q1, Q2, & Q3). This technique allows for target detection of molecules of interest. Ion pairs refers to a parent peptide detected in Q1 in its doubly or triply charged form and a resulting y or b ion as generated by Q2 and detected in Q3 of a triple quadrupole mass spectrometry instrument. SIS internal peptide refers to a synthesized isotopically-labeled peptide with the same sequence as the peptide to be monitored in Q1 and used as an internal standard for reference to quantify the peptide of interest. The −y ion refers to an ion generated from the c-terminal of a peptide fragment. The −b ion refers to an ion generated from the n-terminal of a peptide fragment. Quantitative Ion refers to the selected highest intensity y or b ion used to determine the quantity of its parent protein in a biological sample. Qualitative Ion refers to ion/ions chosen to ensure the integrity of the Qualitative Ion to selected protein of interest and labeled peptide to selected standards.

CLIA refers to Clinical Laboratory Improvements Amendments, which are federal regulatory standards that apply to all clinical laboratory testing preformed on humans in the United States, except clinical trials and basic research. (CLIA related Federal Register and Code of Federal Regulation Announcements), CLIA approved laboratory refers to a clinical lab that preforms laboratory testing on human specimens for diagnosis, prevention, or treatment of disease or impairment and is approved and monitored by a Food and Drug Administration (FDA) approved regulatory organization (CLIA Laws and Regulations, 2013). CLIA-waived test refers to a clinical laboratory test meeting specific criteria for risk, error, and complexity as defined by the FDA.

Point-of-care device refers to an instrument or cartridge available at the location of patient and physician care, which contains binding agents to a biomarker, or series of biomarkers of interest, and which can generate information on the presence, absence, and in some cases concentrations of detected biomarkers. Analyte refers to any measurable biomarker, which can be protein, peptide, macromolecule, metabolite, small molecule, or autoantibody. Biological fluid, as used herein, refers to tears, whole blood, serum, urine, and saliva. Biomarker refers to any substance (e.g. protein, peptide, metabolite, polynucleotide sequence) the concentration level of which changes in the body, for example increased or decreased, as a result of a disease or condition. Marker and biomarker can be used interchangeably used herein.

Lateral flow test refers to a device that measures the presence of an analyte in a biological fluid using porous paper of sintered polymer. ELISA refers to Enzyme-linked immunosorbent assay, which utilizes antibodies or antigens to detect the presence and concentration of an analyte of interest. Diagnostic panel refers to a group of molecules for example proteins or peptides, the combined concentrations of which are used to diagnose a disease state, for example cancer. A breast cancer marker refers to a molecule: for example protein, peptide, metabolite, polynucleotide sequence, the concentration level of which changes in the body: for example increased or decreased, as a result of the presence or absence of cancer.

In addition to being useful to diagnose cancer, and in particular breast cancer, in a subject, kits and methods provided herein can be used to monitor treatment or recurrence of cancer in an individual previously diagnosed with cancer. Thus if the levels of the markers selected from the following and as listed in Table 1: Ig lambda chain V-IV region Hi1 (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (84E1Z4), Alpha-1-antichymotrypsin (AACT), Superoxide dismutase [Cu—Zn] (SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-1 (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-1 region EU (KV106), Alcohol dehydrogenase class 4 mu/sigma chain (ADH7), Protein AMBP (AMBP), Angiotensinogen (ANGT), Antithrombin-II (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT). Glutathione reductase, mitochondrial (GSHR). Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (TH10), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) increases or decreases over time in the same subject after treatment, further chemotherapeutics targeting the cancer can be administered.

Methods and kits can also be used to monitor the effectiveness of a chemotherapeutic treatment. In this alternate embodiment, the levels of the biomarkers selected from the following and as listed in Table 1: Ig lambda chain V-IV region Hi1 (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (SIOAS), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (84E1Z4), Alpha-1-antichymotrypsin (AACT), Superoxide dismutase [Cu—Zn] (SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodtulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-1 (APOA1), Apolipoprotein A-IV (APOA4), Flavin reductase (NADPH) (DLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type H cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (IT1H1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) can increase or decrease over time if the treatment regime is effective and either would not change or can increase or decrease over time if the treatment regime is not effective in a single subject, depending on which biomarker(s) are being examined in the subject.

Treating cancer includes, but is not limited to, reducing the number of cancer cells or the size of a tumor or mass in the subject, reducing progression of a cancer to a less aggressive form, reducing proliferation of cancer cells or reducing the speed of tumor growth, killing of cancer cells, reducing metastasis of cancer cells or reducing the likelihood of recurrence of a cancer in a subject. Treating a subject, as used herein, refers to any type of treatment that imparts a benefit to a subject afflicted with a disease or at risk of developing the disease, including improvement in the condition of the subject for example in one or more symptoms, delay in the progression of the disease, delay in the onset of symptoms, or delay in the progression of symptoms, etc.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second; and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language for example "such as," provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values near to the recited amount are included in that amount, such as values that can or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what that author asserts, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references. Any references mentioned are not admitted to be prior art with respect to the present invention.

The following examples are meant only to be illustrative and are not meant as limitations on the scope embodiments of the invention or of the appended claims.

EXAMPLES

Example 1

Participant Selection

Study participants were recruited from patients being seen at Breast Health and Surgery Centers AR, OK, TN and WA under Institutional Review Board approval. All patients were consented and provided a copy of the informed consent prior to sample collection or completing patient information sheet. Samples were collected by clinic staff (i.e. nurses and technicians) and/or Ascendant Dx staff. Inclusion/exclusion criteria used for patient selection were as follows:

Inclusion Criteria:
  Individuals between the ages of 18-100 years of age,
  Presenting for a routine check-up, or
  Presenting for the evaluation of an abnormal exam or test, or
  Presenting for the evaluation of palpable mass, or
  Presenting with a mass pre or post biopsy as long as a portion of the mass is remaining, or
  Have recently been diagnosed with breast cancer but have not undergone treatment of any kind.

Exclusion Criteria:
  Individuals below the age of 18 or over 100
  Experiencing a concurrent eye infection or trauma, or
  Currently experiencing acute conjunctivitis, or
  Have been diagnosed with breast cancer and have undergone treatment.

Control samples were collected from patients being seen for routine screening mammograms and did not receive a call back for additional procedures. Benign samples were collected at the time of biopsy and were included in the benign group once the pathology results were determined. Cancer samples were also collected at time of biopsy and included in the cancer group after pathology results were known, from patients having MRI's prior to surgery, and from patients undergoing sentinel node procedures prior to surgery.

Data collected from participants included the following: age, sex, race, currently taking birth control or on hormone replacement therapy, ophthalmological infections, current or recent chemotherapy treatments, family history of cancer, genetic testing (BRAC1/2) if available, cancer stage (I, II, III, IV), cancer type (Ductal Carcinoma In Situ, Invasive Ductal Carcinoma, Invasive Lobular Carcinoma, Lobular Carcinoma In Situ, and Unknown), hormone receptor status (ER+/−, PR+/−, HER2+/−), size of mass, tumor grade (I, II, III), breast density score (densities identified as category 1, 2, 3, or 4) and previous history of cancer.

Example 2

Schirmer Strip Sample Collection Procedure

Institutional review board approval was obtained for the collection of tears using Schirmer strips (Gulden Opthalmics Elkins Park, PA). For collection, the rounded tip of the Schirmer strip was folded over at the 0 mm line forming a lip. The folded portion was placed in the lower eyelid of the participant and they were asked to close their eye and keep it in the closed position for a period of 5 minutes. After five minutes the strip was removed and placed in a sterile 1.5 mL pre-labeled snap top tube and placed at −20° C. or −80° C. depending on availability. Collection criteria stated that if the 35 mm mark was reached prior to the five minute time, the strip can be removed. Samples collected at participating clinics were retrieved by Ascendant Dx staff on a weekly basis and transferred on-dry ice to Ascendant Dx's laboratory facility.

Example 3

Schirmer Strip Sample Processing

Protein elution was carried out by first dicing the strips, using sterile tweezers and scissors, into clean sterile 1.5 mL snap top tube. 200 μL of 1× Phosphate-buffered saline (PBS) was added to the diced strip and the sample was incubated at 4° C. with mild shaking for 3 hours. Following elution, the samples were spun briefly in a tabletop centrifuge to collect the strip fragments at the bottom of the tube, and the supernatant was transferred to a new clean 1.5 mL snap top tube. Total protein content was determined using standard bicinchoninic acid (BCA) assay, and the samples were stored at −80° C. until further use.

Total protein content of each pool was determined using a BCA assay kit (Pierce) with a 1:20 (v/v) ratio of standard and unknown to working reagent and an incubation time of 30 min at 37° C. To ensure reliable total protein content calculation, a series of dilutions were made for each sample, for example 1:2, 1:4, 1:6, and all dilutions were plated in triplicate. A standard curve using diluted albumin (2 mg/ml, 1.5 mg/ml, 1 m/ml, 0.75 mg/ml, 0.5 mg/ml, 0.25 mg/ml 0.125 mg/ml 0.025 mg/ml and 0 mg/ml) was generated and blank subtraction was applied to all standards and unknowns. The protein concentration for each unknown was calculated using a four-parameter fit of the standard curve. Concentrations were multiplied by the dilution factor and averaged to give an accurate total protein content calculation. Assays were considered valid if the coefficient of variation (% CV) was 15% or below.

Example 4

Methods and Results for Label Free Quantitation by LC MS/MS

Experiment 1: In solution trypsin digestion followed by LC MS/MS was carried out on 25 breast cancer samples, 25 benign samples, and 25 control samples by the Proteomic Core at the University of Arkansas for Medical Sciences (UAMS). Solution digests were carried out on all 75 samples in 100 mM ammonium bicarbonate (Sigma-Aldrich), following reduction in 10 mM Tris[2-carboxyethyl]phosphine (Pierce) and alkylation in 50 mM iodoacetamide (Sigma-Aldrich), by addition of 100 ng porcine trypsin (Promega) and incubation at 37° C. for 12-16 hours. Peptide products were then acidified in 0.1% formic acid (Fluka). Tryptic peptides were separated by reverse phase Jupiter Proteo resin (Phenomenex) on a 100×0.075 mm column using a nanoAcquity UPLC system (Waters). Peptides were eluted using an 80 min gradient from 97:3 to 35:65 buffer A:B ratio. [Buffer A=0.1% formic acid, 0.05% acetonitrile; buffer B=0.1% formic acid, 75% acetonitrile.] Eluted peptides were ionized by electrospray (1.8 kV) followed by MS/MS analysis using collision-induced dissociation on an LTQ Orbitrap Velos mass spectrometer (Thermo). MS data were acquired using the FTMS analyzer in profile mode at a resolution of 60,000 over a range of 375 to 1500 m/z. MS/MS data were acquired for the top 15 peaks from each MS scan using the ion trap analyzer in centroid mode and normal mass range with a normalized collision energy of 35.0. Proteins were identified from MS/MS spectra by database searching the Mascot search engine (Matrix Science) or MaxQuant quantitative proteomics software (Max Planck Institute). Mascot search results were compiled using Scaffold (Proteome Software).

The following criteria were set to select a group of proteins that can be indicative of altered breast physiology: 1) protein has a fold change of 1.5 or greater (in either positive or negative direction with respect to cancer). 2) fold change should be accompanied by p value of <0.05. 3) protein is present in 12 out of the 25 cancer samples. Using these criteria, the list of over 500 was reduced to the following proteins: Alpha-1-antitrypsin (A1AT), Antileukoproteinase (SLP1), Cofilin (COF1), Antithrombin-III (ANT3), Beta-2-microglobulin (B2MG), Protein-glutamine-gamma-glutamyltransferase (B4DIT7), Uncharacterized protein (B8ZZQ6), Calmodulin-like protein 5 (CALL5), Cystatin-B (CYTB), Neutrophil defensing-1 (DEF1), Destrin (DEST), Kaliocin-1 (E7ER44), Cluster of Rab GDP dissociation inhibitor beta (E7EU23), Elongation factor 1-alpha (EF1A1), Ezrin (EZR1), Heme-binding protein 2 (HEB2), Heat Shock cognate 71 (HSP7C), Heat shock protein beta 1 (HSPB1), Ig Heavy chain V-III (HV303), Cluster of Ig Heavy chain V-III region BRO (HV305), Lipocalin-1 (LCN1), Galectin-3 (LEG3), Ig lambda chain V-IV (LV403), Isoform 2 of Ig mu chain c region (P01871), Cluster of isoform 2 heat shock protein (P07900-2), Cluster of 14-3-3 protein zeta delta (P63104), Isoform 3 of Perilipin-3 (PLIN3), Proteasome activator complex subunit 1 (Q06323), UMP-CMP kinase (Q5T0D2), Protein S100-A4 (S10A4), S100-A8 (S10A8), Protein S100-A9 (S10A9), Protein S100-A11 (S10AB), Submaxillary gland androgen-regulated protein (SMR3B), Zinc-alpha-2-glycoprotien (ZA2G), Zymogen granule protein 16 homolog B (ZG16B).

Experiment 2: In solution trypsin digestion followed by LC MS/MS was repeated using fifty samples in each group (breast cancer, benign, control). Identical methods as described for Experiment 1 were used for Experiment 2. The increase in samples size caused some of the trends observed in Experiment 1 to disappear, while making trends emerging in Experiment 2 more prominent in Experiment 2. From this data the list of 500 proteins described in Experiment 1 was further refined down to 103 proteins of interest. This list includes: Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-II region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (ALIA1), Uncharacterized Protein (B4E1Z4), Alpha-1-antichymotrypsin (AACT), Superoxide dismutase [Cu—Zn] (SODC), SPARC-like protein 1 (SPRL1), Ig heavy chain V-II region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9P1T3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (13L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-H (APOA2), Calpastatin (B7Z574), Brain acid soluble protein 1 (BASP1), Alpha-2-HS-glycoprotein (C9JV77), Caireticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type 1.1 cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1). Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) (Appendix 1). The complete list of proteins identified was exported from Scaffold software for analysis using JMPpro11 statistical software package.

Example 5

Statistical Analysis Using JMPpro11 Software

Experiment 1: The data was organized by using Microsoft Excel® spreadsheet software with spectral intensities of each of the previously identified proteins for all 75 samples. Also included in the spreadsheet were sample status (cancer, benign, control) cancer type, tumor size grouping (1=0.1 mm-1 cm, 2=1.1-2.9 cm, 3=3 cm or greater) and tumor grade status. This spreadsheet was uploaded into the JMPpro11 software package for analysis.

Binary linear regression was applied between cancer and control samples. Six proteins were identified as significant based on their sigmoidal curve and p-value, they were Ig lambda chain V-IV (LV403), Ig heavy chain V-III region BRO (HV305), Ig heavy chain V-III VH26 (HV303), Lipocallin-1 (LCN1), Beta-2-microglobulin (B2MG), Zinc-alpha-2-glycoprotein (ZA2G). All six proteins appeared to be down-regulated with respect to cancer. To determine if the down regulation of these proteins was specific to breast cancer a binary linear regression was repeated between benign and control. This comparison indicated the six previously identified proteins were also down-regulated in benign samples and an additional four proteins were identified as significant between benign and control; Antileukoproteinase (SLP1), Calmodulin-like-protein 5 (CALL5), Cystatin B (CYTB), and Galectin-3 (LEG3).

Nominal logistic regression was carried out using all three groups and all ten proteins to determine degree of differentiation between all groups. Degree of misclassification was for the group of ten proteins was 12%. Receiver operator curves for each category produced AUC values of 0.96 for cancer, 0.94 for benign, and 0.98 for control (FIG. 1). One way ANOVA analysis was preformed to ensure a shifting mean value for the three categories of samples by each protein (FIG. 3).

Experiment 2: One-way ANOVA analysis was preformed using spectral intensities recorded for all proteins identified from mass spectrometry. Tryptic peptide products were analyzed for all proteins. Proteins were compared in three ways: 1) control vs cancer, 2) cancer vs benign, 3) benign vs control. An alpha level of 0.05 was used as an indicator of significant expression change between the groups. Variations in spectral intensities of tryptic fragments were compared. A series of proteins was identified where expression level increased in breast cancer samples with respect to control. Proteins were also identified where expression decreased in breast cancer samples with respect to control. To ensure experimental validity, it was established that proteins were present in whose expression remained constant across all groups tested (FIG. 4).

The initial list of 500 proteins was reduced to 103 proteins of interest. Within this group of proteins are proteins with increased expression with respect to breast cancer as well as proteins with decreased expression with respect to breast cancer (FIG. 4). The diagnostic capability of whole protein sequence, tryptic peptides, and sequence anomalies, which can be present as a result of disease, are all of interest.

Example 6

ELISA Analysis

A series of proteins with an increase in expression level in cancer samples relative to control samples were observed by mass spectrometry, and several candidates were selected for further validated using ELISA. S100A9 was selected as a representative example of increased expression in tears of breast cancer patients relative to control. LG3BP is shown as a representative of proteins with a decreased expression level in breast cancer samples relative to control samples. Standard ELISA protocol was used to evaluate the expression level of in tears. Data for S100A9 and LG3BP was obtained using kits purchased as DuoSets from R&D Systems (Minneapolis, MN). ELISA procedures were carried out according to instructions provided by R&D systems. Briefly, 100 µL per well of capture antibody, diluted to the recommended working concentration (GAL3BP 1.0 ug/ml; S100A9 0.5 ug/mi) in 1×PBS, was added to a high binding 96 well plate and incubated overnight (~16 hrs) at room temperature. The plate was rinsed with 1×PBS with 0.05% Tween four times, and blotted against clean absorbent paper to remove any traces of liquid following each rinse. Rinse cycles were carried out after each step of the assay. Blocking buffer (1×PBS with 1% BSA) was added to all wells (~200 µL/well) and the plates were incubated for two hours at room temperature. Tear samples were diluted using 1×PBS with 1% BSA at dilutions of 1:10 and 1:50 for S100A9 and 1:100 & 1:500 for Galectin 3 Binding Protein. Dilutions known to fall within the linear region of the standard curve for each assay were selected based on results from previous optimization assays. Samples and standards were tested in duplicate using 100 µL/well and incubated at room temperature for 2 hours. Detection antibody was diluted to the recommended working concentration (GAL3BP 2 ug/ml and S100A9 1 ug/ml) 100 µL was added to each well, and the plate was allowed to incubate for 2 hours at room temperature. Streptavidin-HRP solution was added to each well (100 µL/well) and allowed to incubate for 15 min at room temperature. Visualization was achieved by addition of TMB substrate solution. After 15 minutes, 50 µL of 1M $H_2SO_4$ was added to each well, and the absorbance at 450 nm was determined. ELISA data was analyzed using Prism version 6.0 available from GraphPad.

Figure 5:
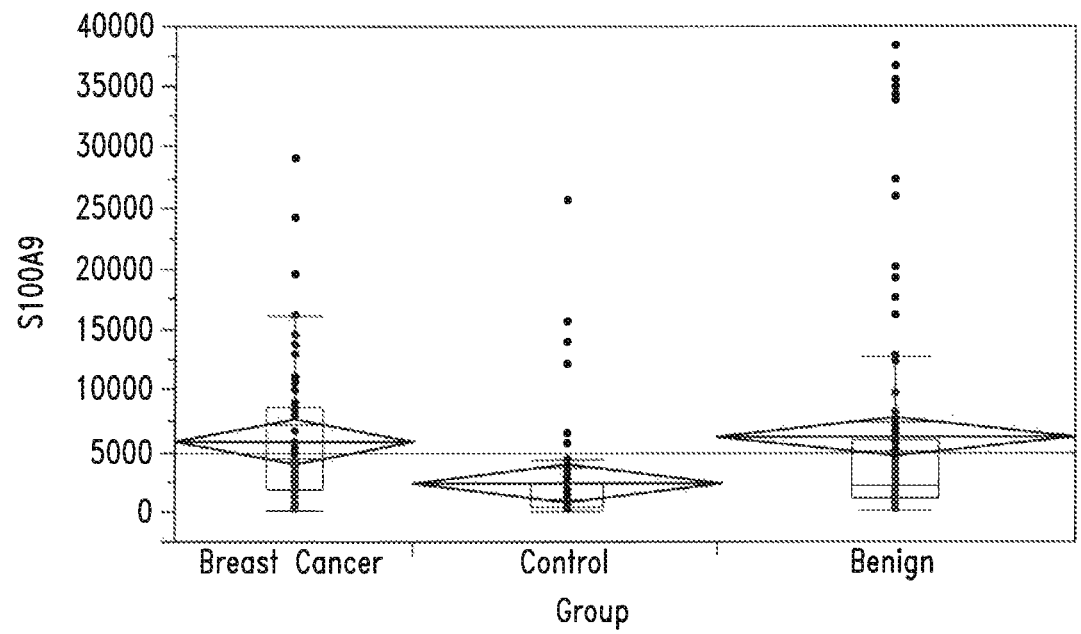
FIG. 5: ANOVA comparing expression levels of S100A9, as determined by ELISA, in breast cancer and control samples.
Figure 6:
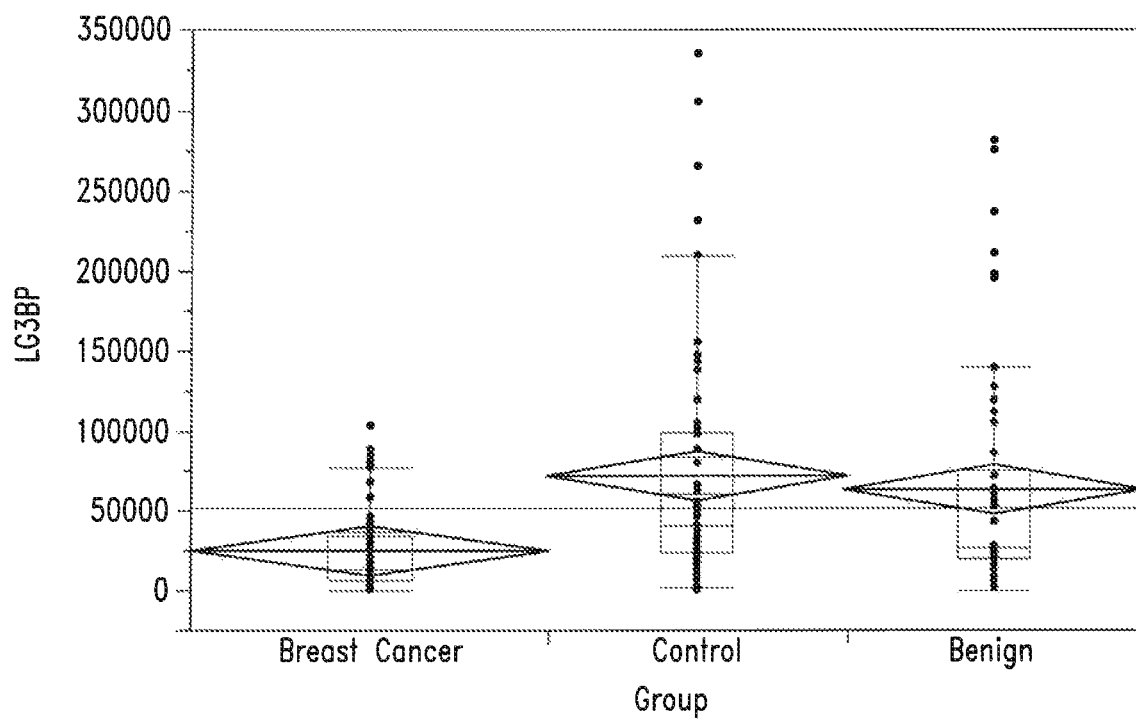
FIG. 6: ANOVA comparing expression levels of LG3BP, as determined by ELISA, in breast cancer and control samples.

Statistical analysis of ELISA data: Concentrations of each protein, as calculated by Prism software, were exported into JMP Pro11 for statistical evaluation. Numerous candidates were selected to be investigated using ELISA assays on Control, Cancer or Benign samples. Results of two proteins (S100A9 and Galectin-3-Binding Protein) are shown (FIG. 5 and FIG. 6, respectively) to provide representative example of increased and decreased protein expression in breast cancer tear samples with respect to control. ANOVA of S100A9 for 63 breast cancer samples, 79 control samples, and 92 benign samples resulted in a p-value of 0.0005 when all three groups were evaluated. Group means for S100A9 were: breast cancer=5673.02 pg/mi; control=2130.18 pg/ml; benign=6179.10 pg/ml. S100A9 expression is increased by 2.6 fold in cancer samples compared to control samples and 2.9 fold increase in benign samples compared to control. ANOVA of Galectin-3 Binding Protein for 66 breast cancer samples, 55 control samples, and 54 benign samples resulted in a p-value of <0.0001 when all three groups were evaluated. Group means for LG3BP were: breast cancer=24448.1 pg/ml; control=70242.2 pg/ml; benign=62329.7 pg/ml. LG3BP has a 2.8 fold increase in control samples compared to cancer samples and a 2.5 fold increase in benign samples compared to cancer.

Figure 7:
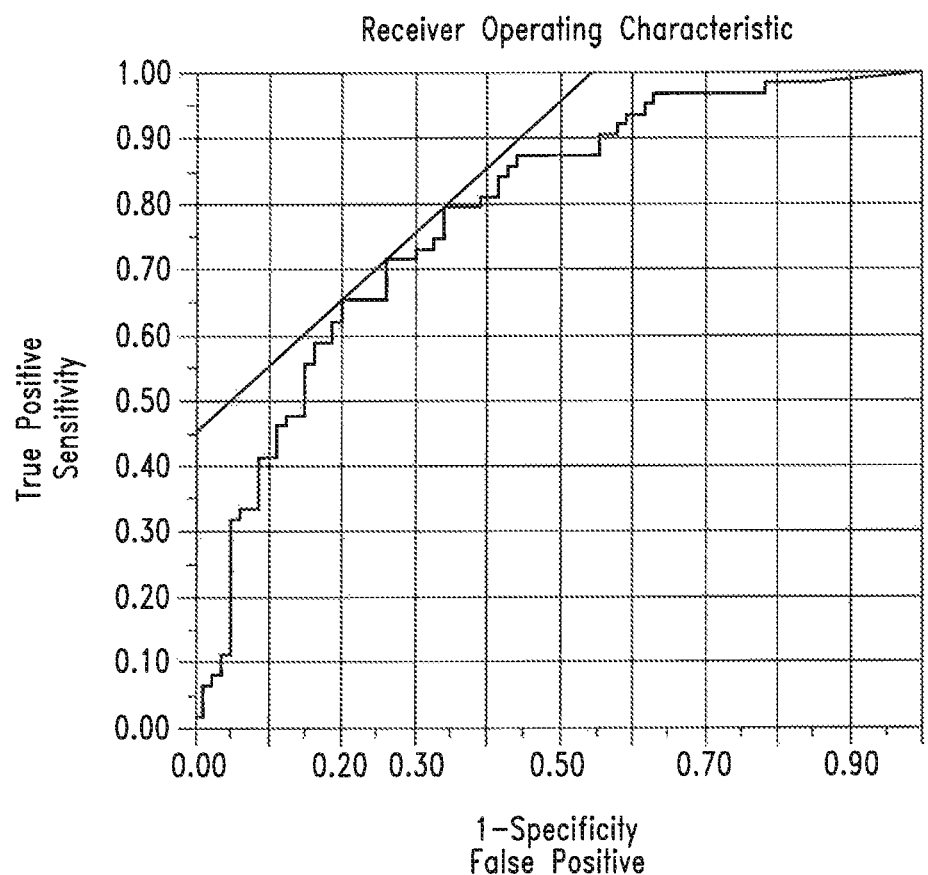
FIG. 7: ROC curve for S100A9
Figure 8:
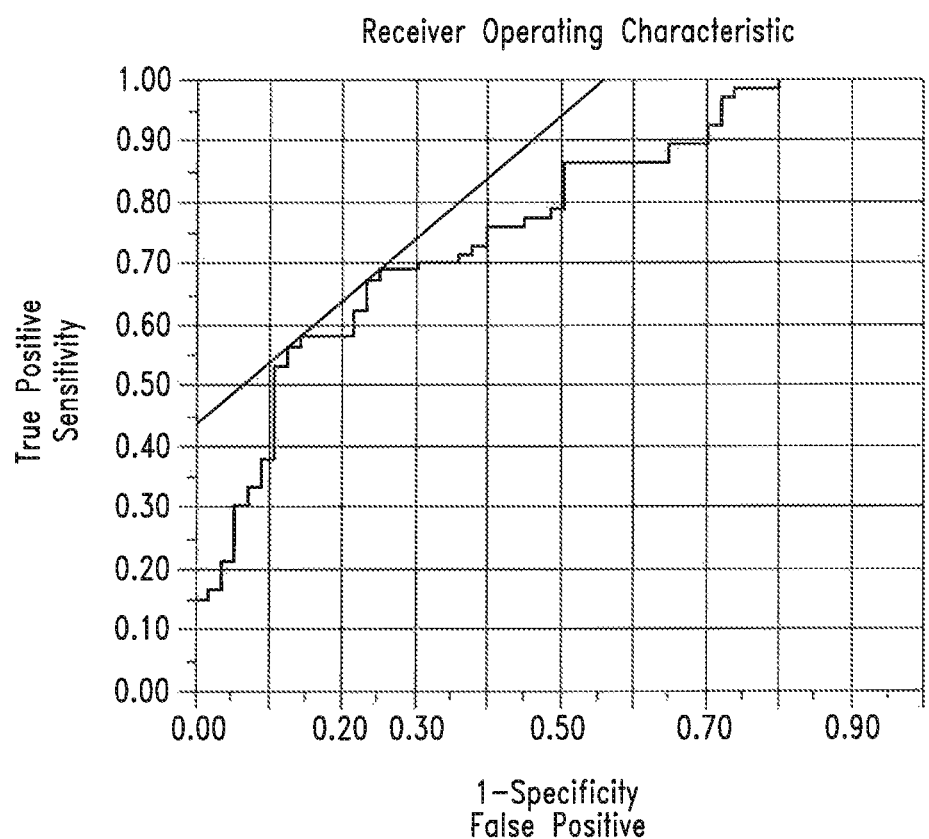
FIG. 8: ROC curve for LG3BP
Figure 9:
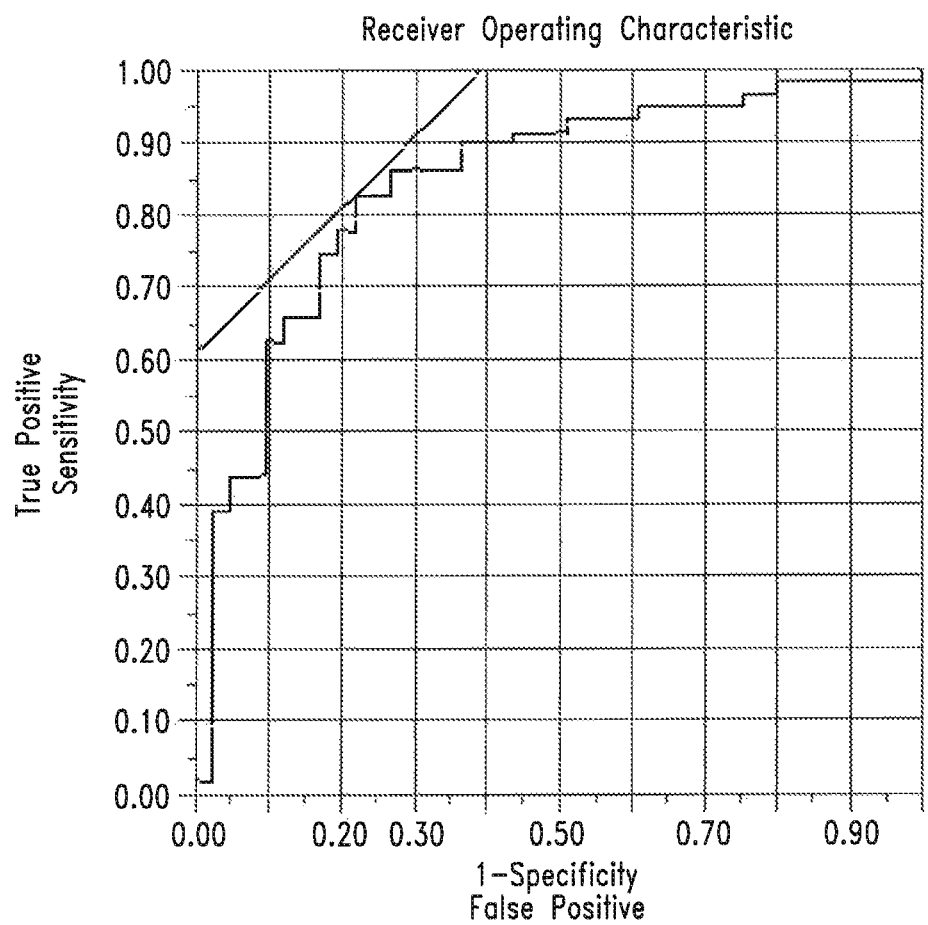
FIG. 9: ROC curve of S100A9 and LG3BP combined.

Nominal logistic regression analysis for breast cancer and control samples, was conducted using the two representative proteins. The generated ROC curve for S100A9 has an AUC of 0.78220 (FIG. 7), and LG3BP has an AUC of 0.76088 (FIG. 8). The analysis was repeated using two proteins and an AUC of 0.84250 was obtained (FIG. 9).

Sample population characteristics: Clinical data such as breast density, cancer type, and tumor size were obtained on as many samples as possible.

Figure 2:
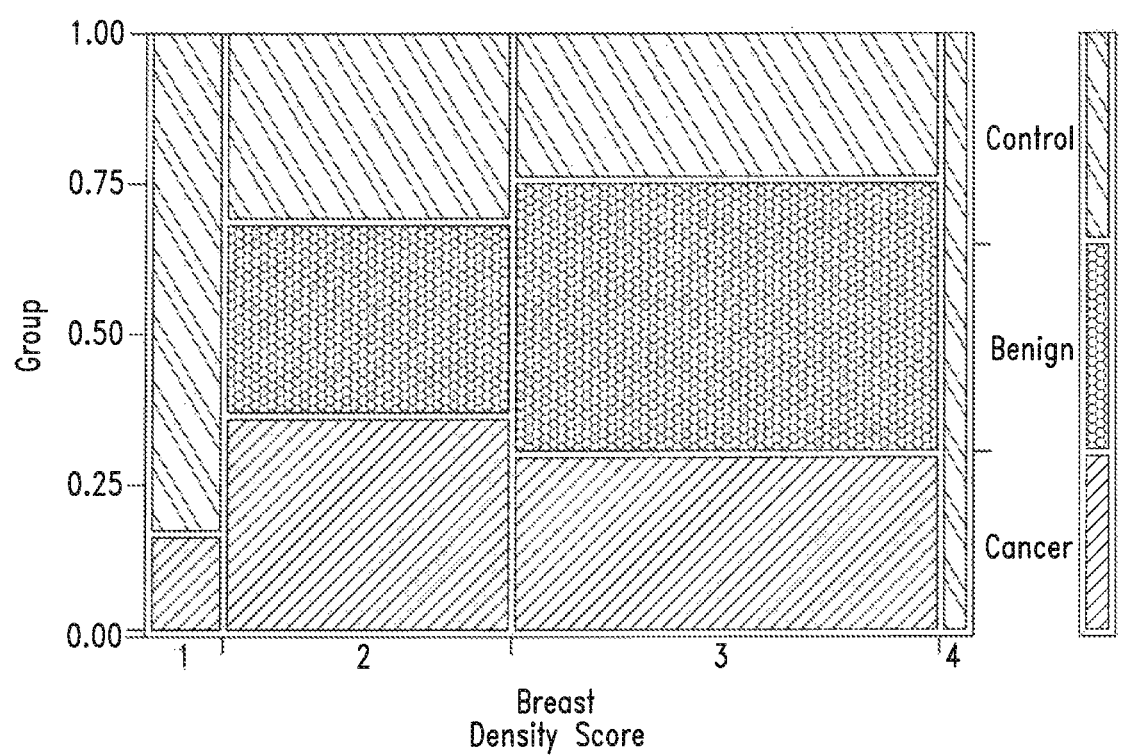
FIG. 2: ROC curves for cancer, benign, and control, from Experiment 1, using Ig Heavy Chain V-IV region HiL, Ig Heavy Chain region V-III region BRO, Ig Heavy Chain V-III region VH26, Antileukoproteinase, β2 Microglobulin, Calmodulin like protein 5, Lipocalin 1, Cystatin B, Galectin 3, Zinc-α 2 glycoprotein.
Figure 3A:
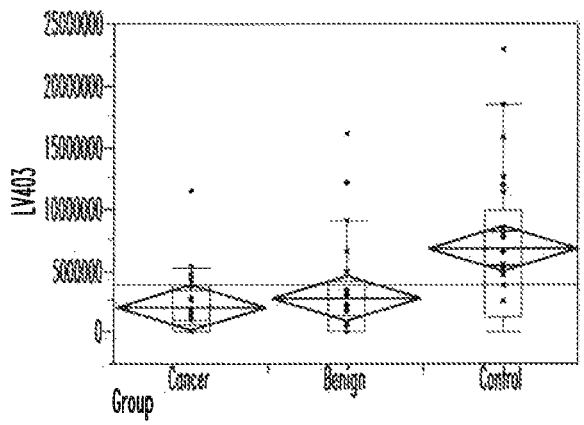
FIGS. 3A-3J: Mosaic plot of the distribution of breast density for 66 of the 75 samples tested in Experiment 1.
Figure 3B:
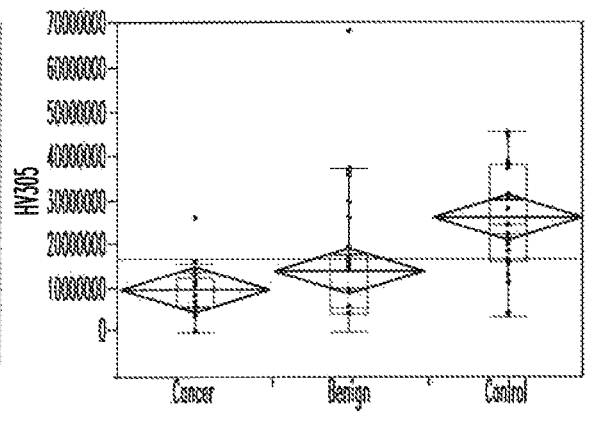
Figure 3C:
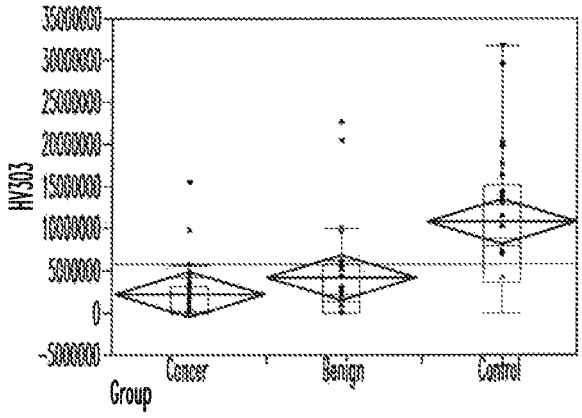
Figure 3D:
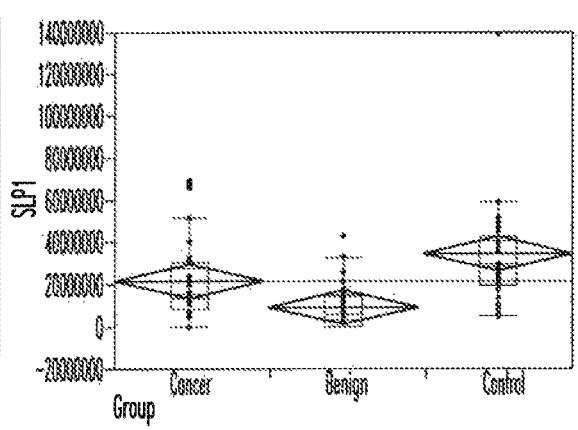
Figure 3E:
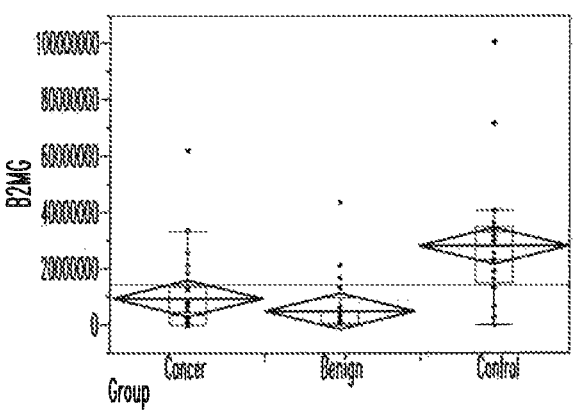
Figure 3F:
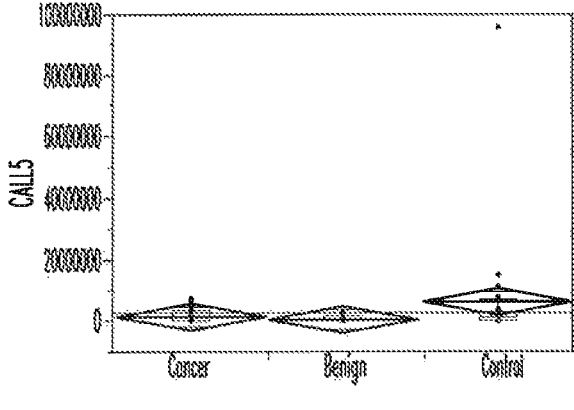
Figure 3G:
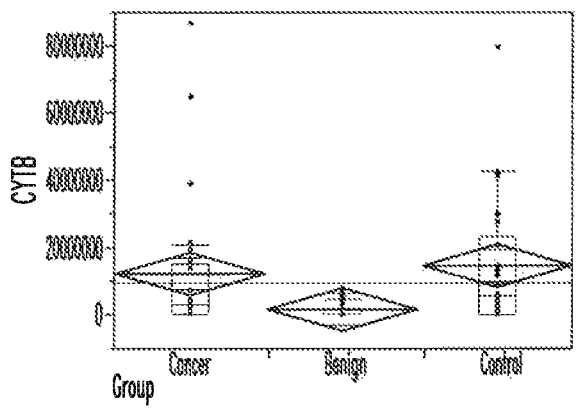
Figure 3H:
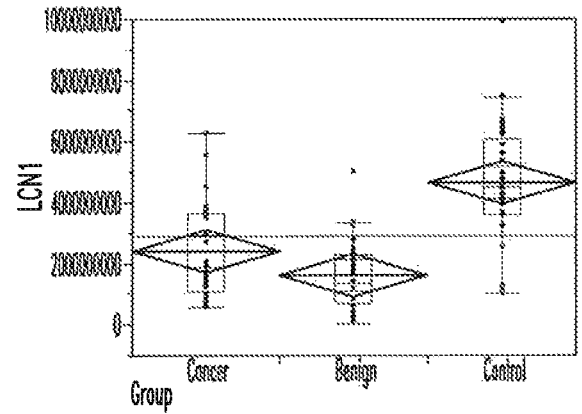
Figure 3I:
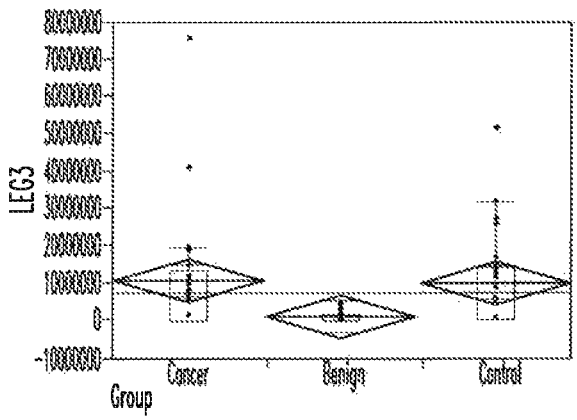
Figure 3J:
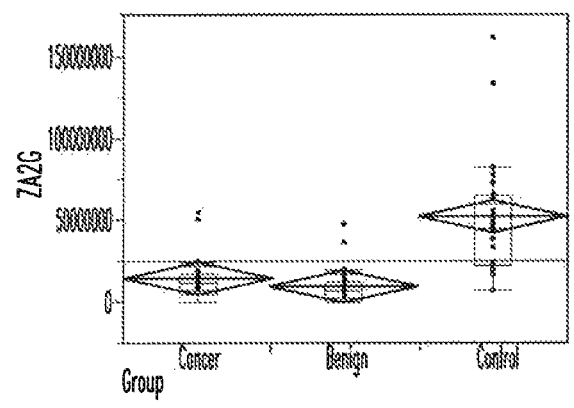
Figure 4A:
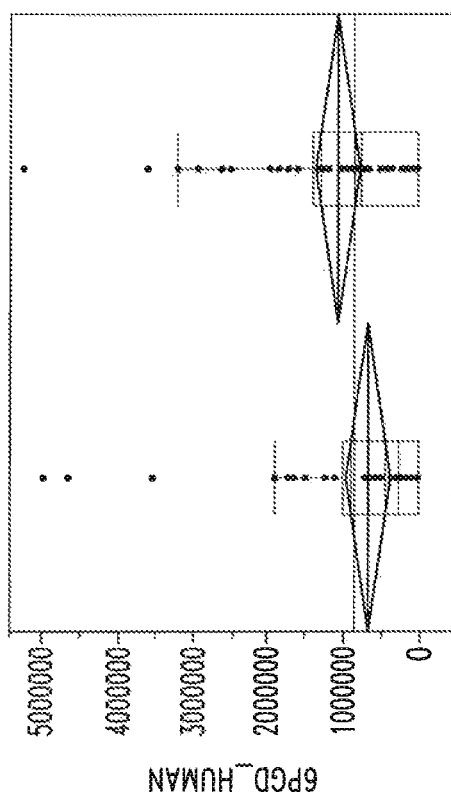
FIGS. 4A-4FF: ANOVA of spectral intensities for proteins identified in Experiment 2. Proteins shown are: (A) 14-3-3 protein sigma (B) 6-phosphogluconate dehydrogenase, decarboxylating (C) Alpha-actinin-4 (D) Retinal Dehydrogenase (E) Argininosuccinate synthase (F) Beta-2-microglobulin (G) Calmodulin (H) Ceruloplasmin (I) Cofilin (J) Cystatin-SN (K) Enolase 1 (L) Gelsolin (M) Heat shock protein beta-1 (N) Ig alpha-1 chain C region (O) Lacritin (P) Lysozyme (Q) Basement membrane-specific heparin sulfate proteoglycan core protein (R) Polymeric immunoglobulin receptor (S) Profilin 1 (T) S100A8 (U) S100A9 (V) Secretoglobin family ID member 1 (W) VEGF coregulated chemokine 1 (X) Histidine triad nucleotide-binding protein 1 (Y) Definsin 1 (Z) L-lactate dehydrogenase A chain (AA) SPARC-like protein 1 (BB) Annexin 5 (CC) Ig heavy chain V-III region TIL (DD) Inter-alpha-trypsin inhibitor heavy chain 1 (EE) Alpha-1B-glycoprotien (FF) Alpha-1-antitrypsin.
Figure 4B:
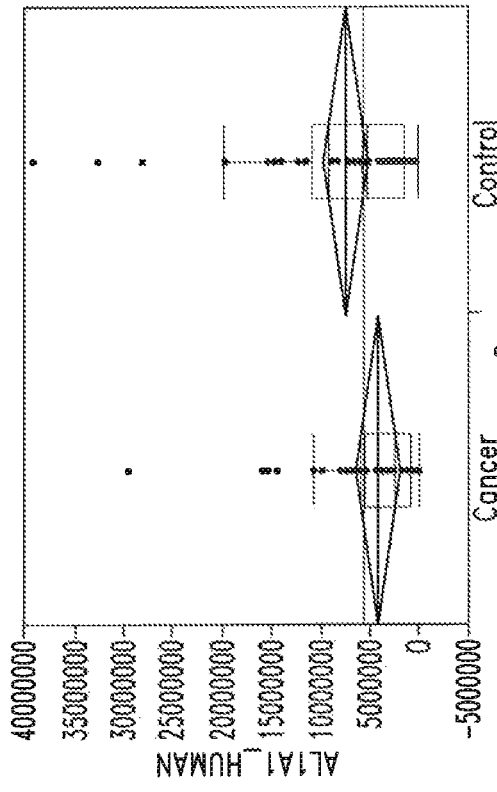
Figure 4C:
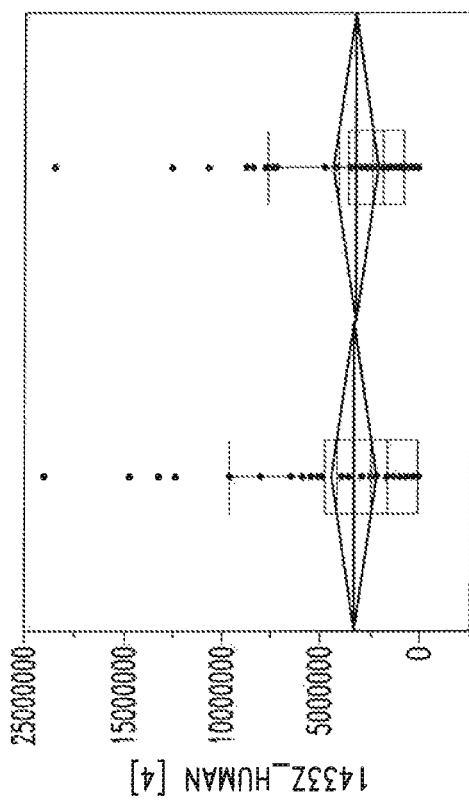
Figure 4D:
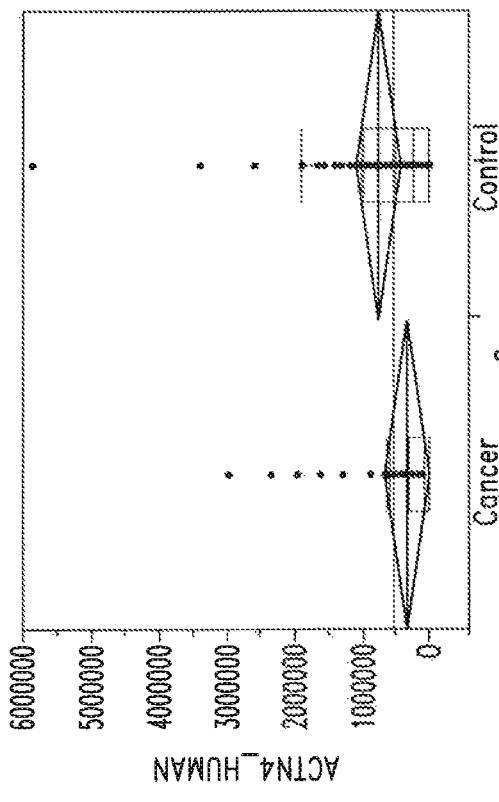
Figure 4E:
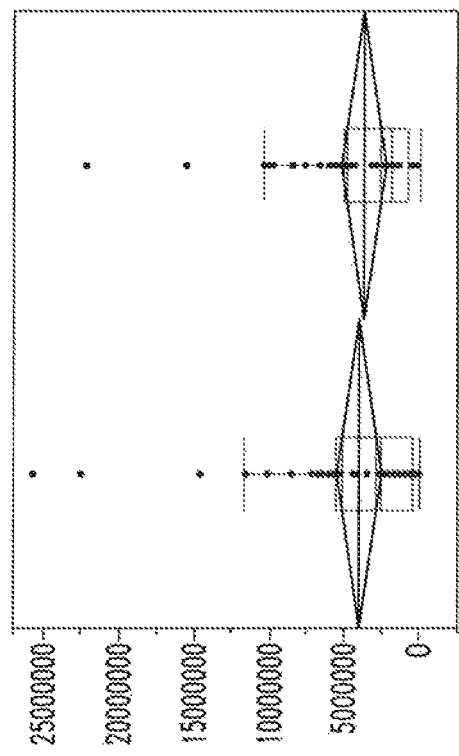
Figure 4F:
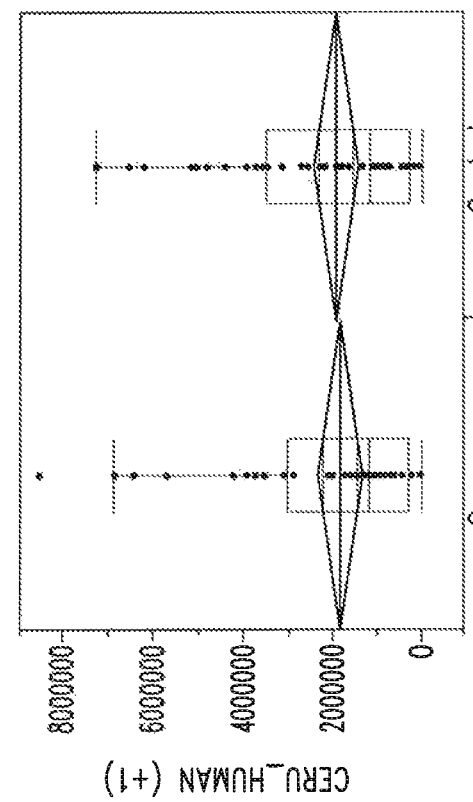
Figure 4G:
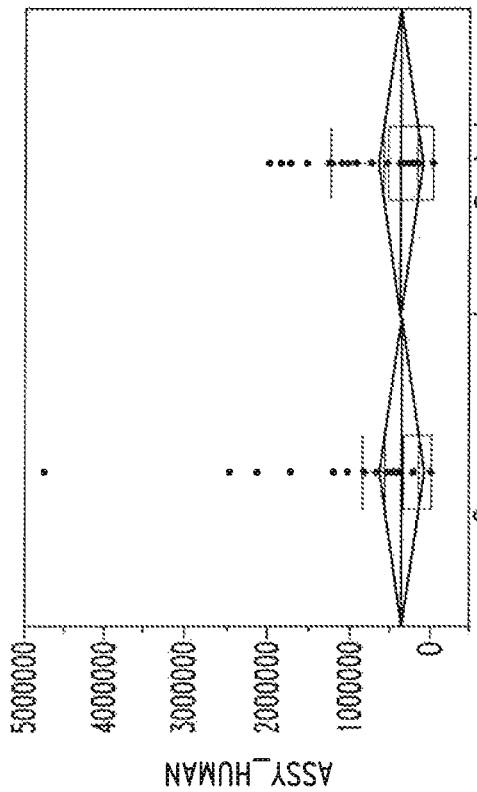
Figure 4H:
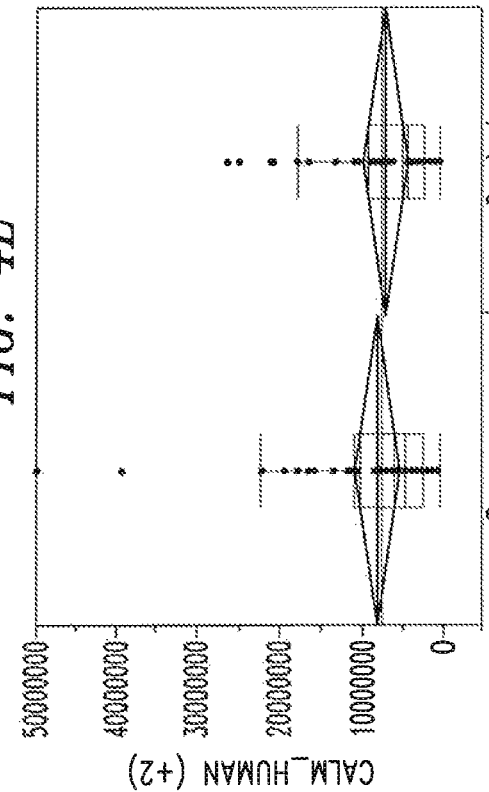
Figure 4I:
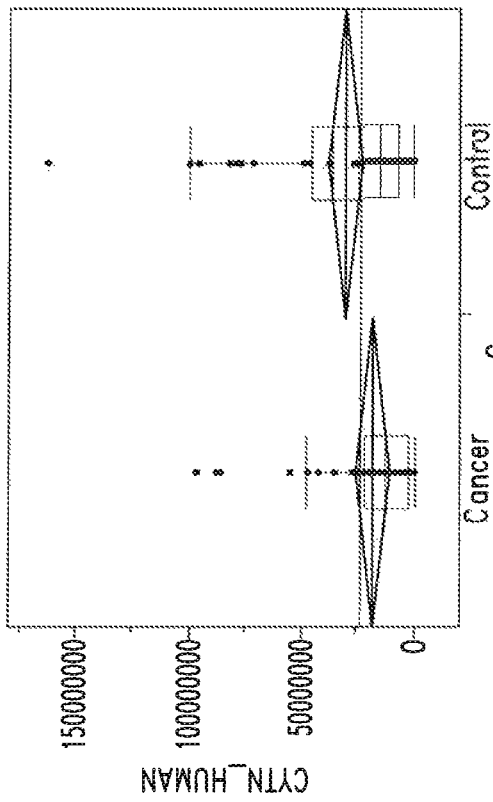
Figure 4J:
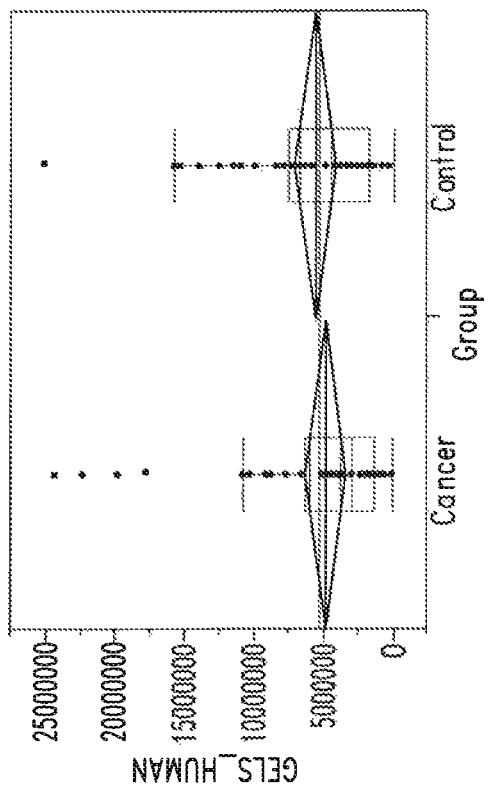
Figure 4K:
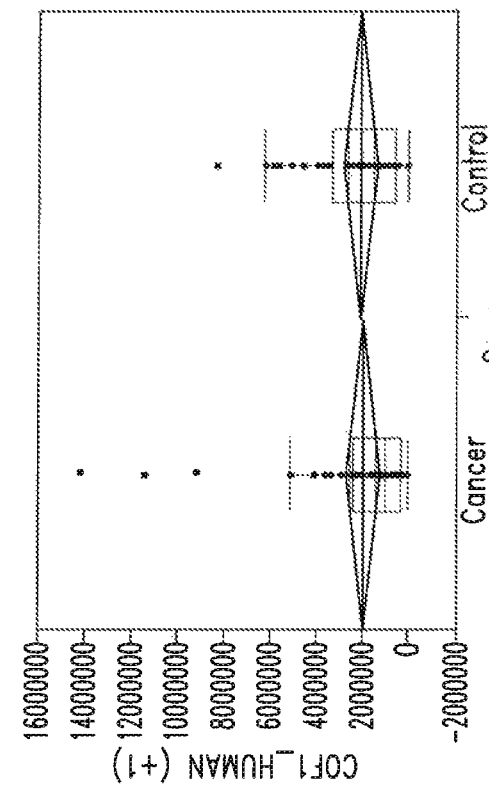
Figure 4L:
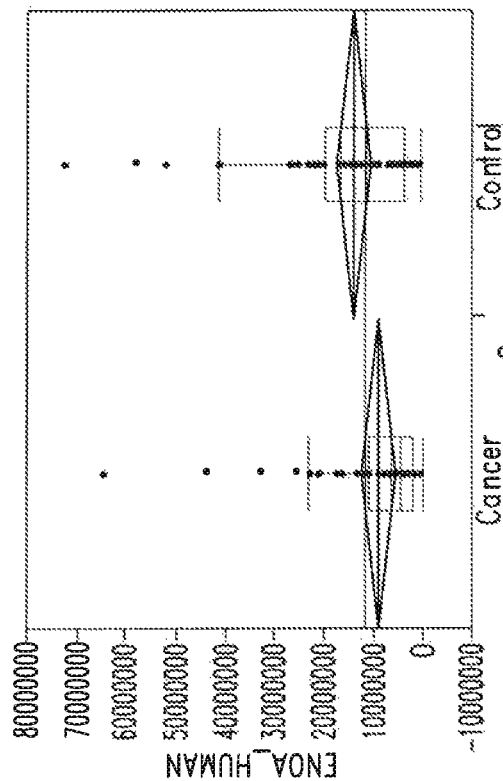
Figure 4M:
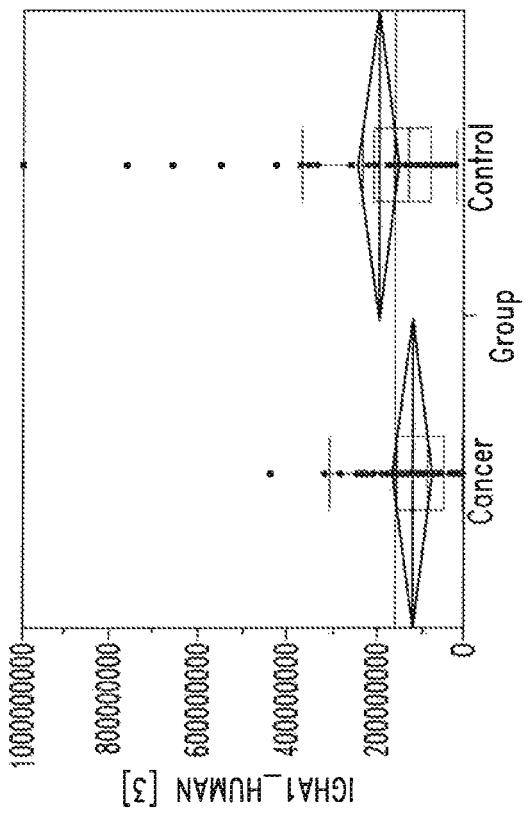
Figure 4N:
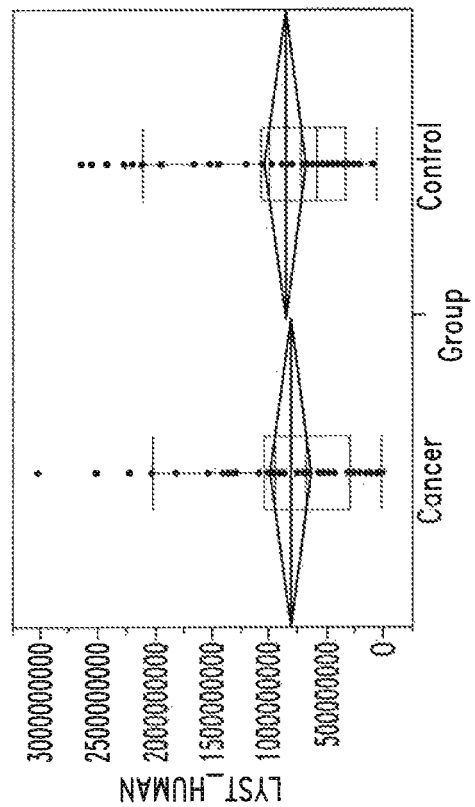
Figure 4O:
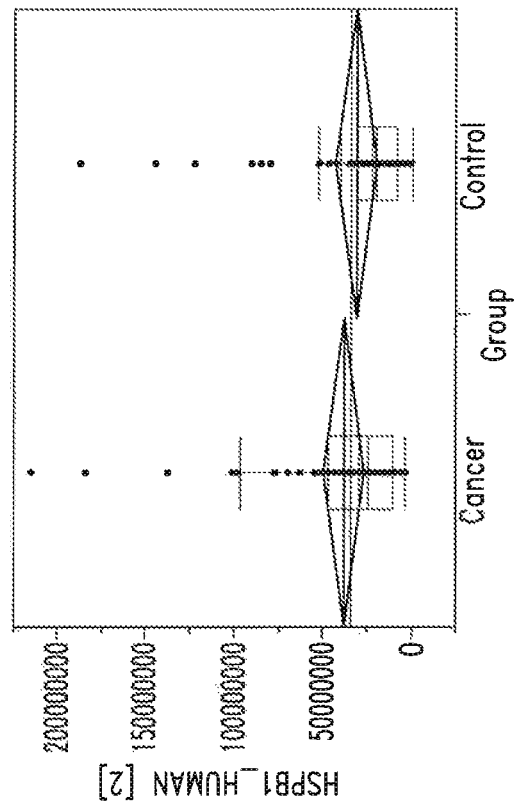
Figure 4P:
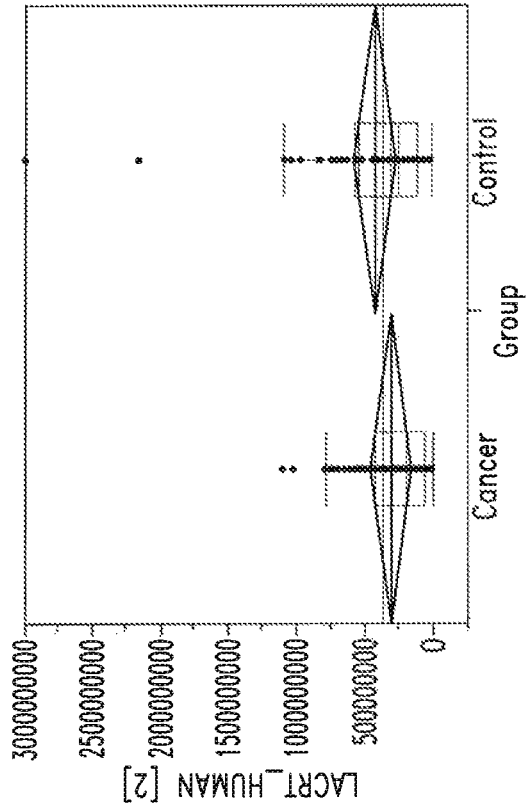
Figure 4Q:
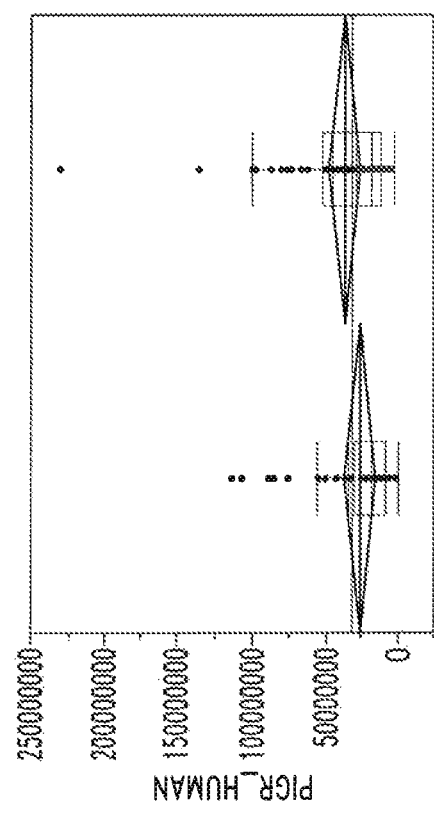
Figure 4R:
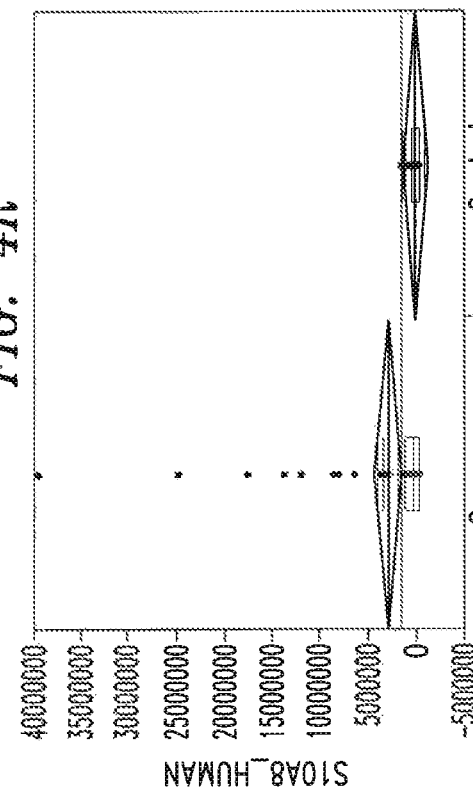
Figure 4S:
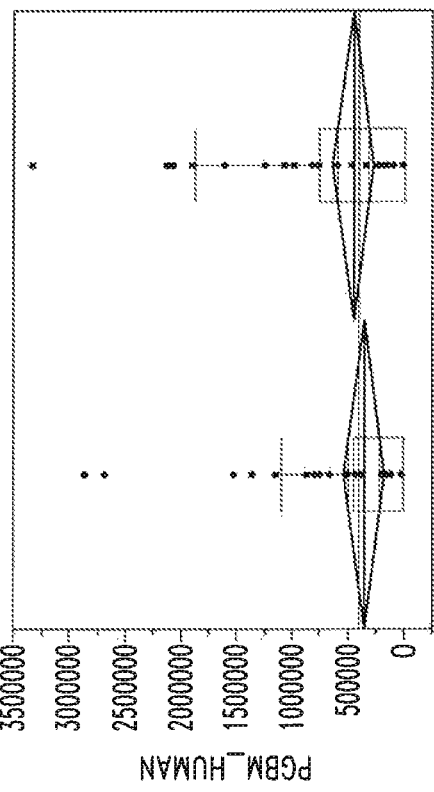
Figure 4T:
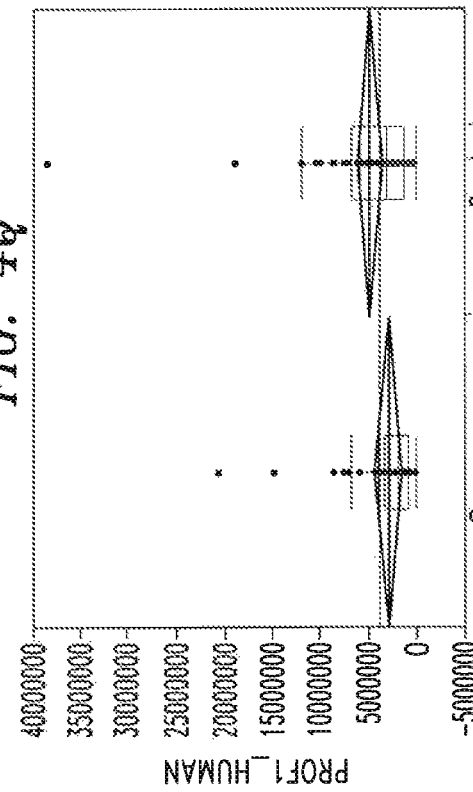
Figure 4U:
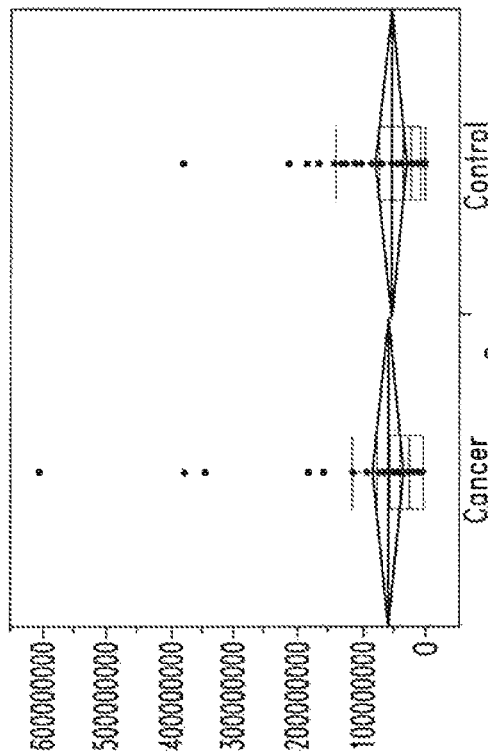
Figure 4V:
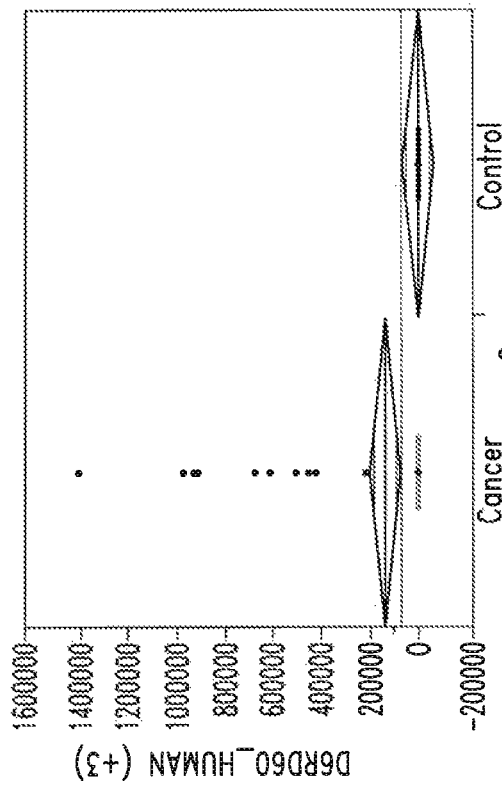
Figure 4W:
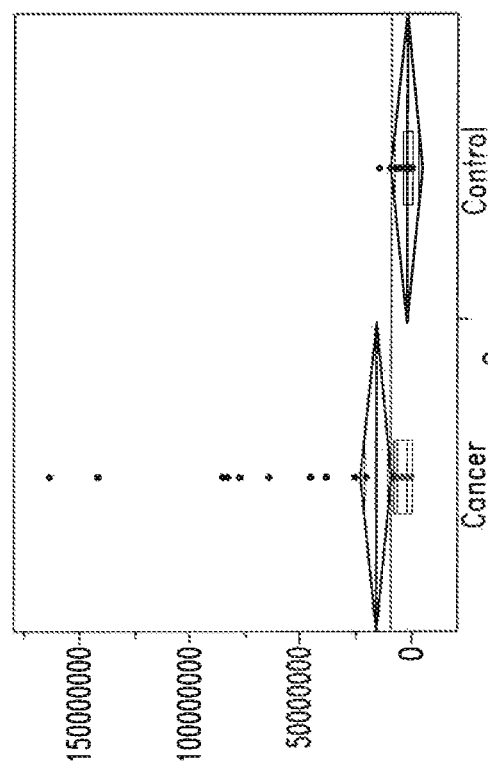
Figure 4X:
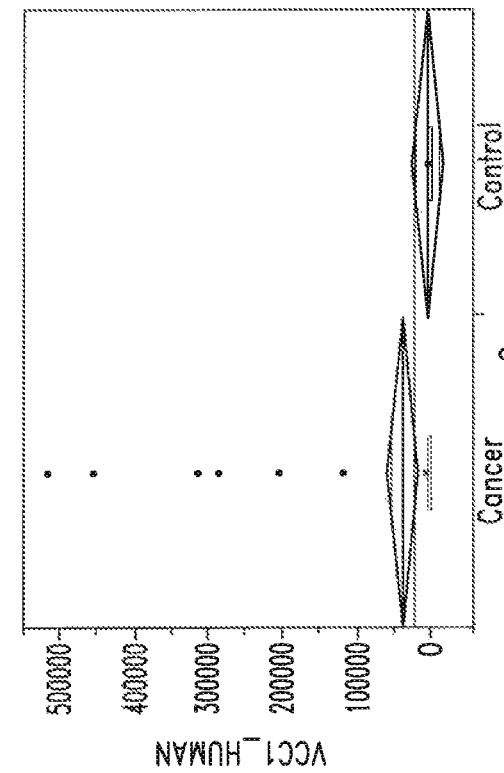
Figure 4Y:
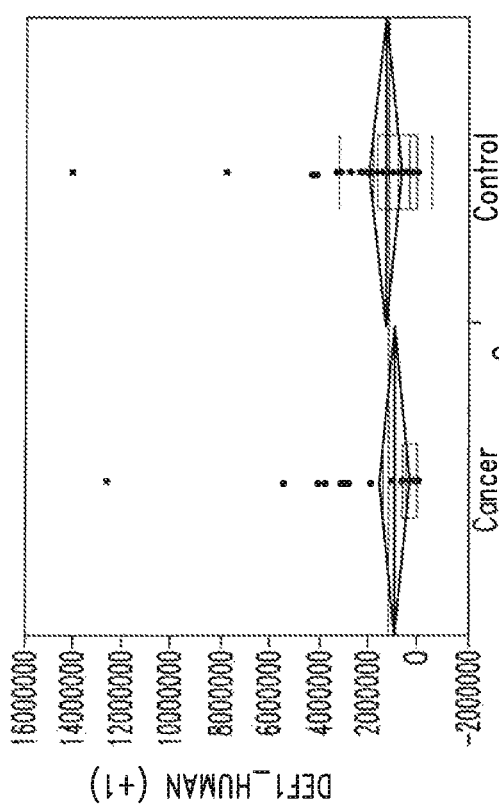
Figure 4Z:
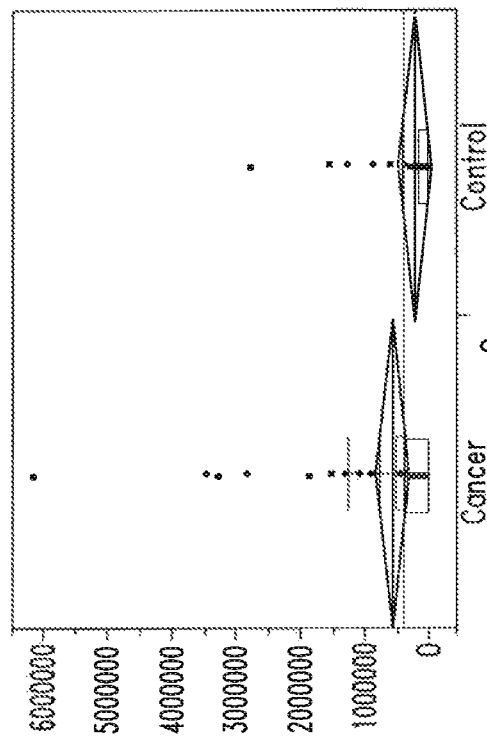
Figure 4A:
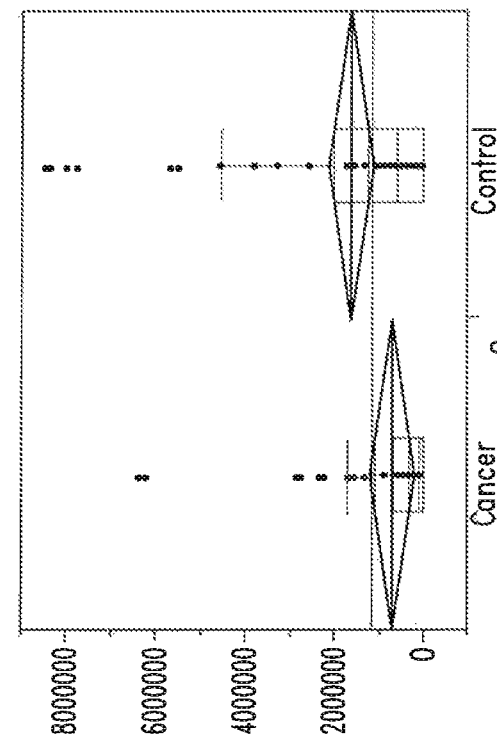
Figure 4B:
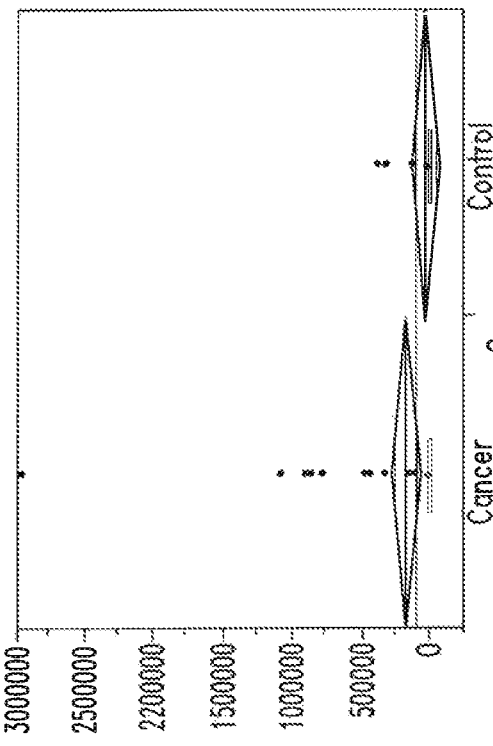
Figure 4C:
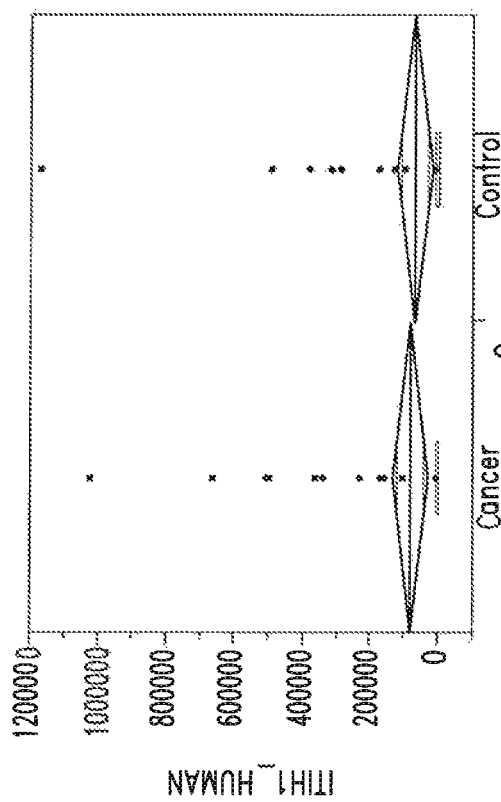
Figure 4D:
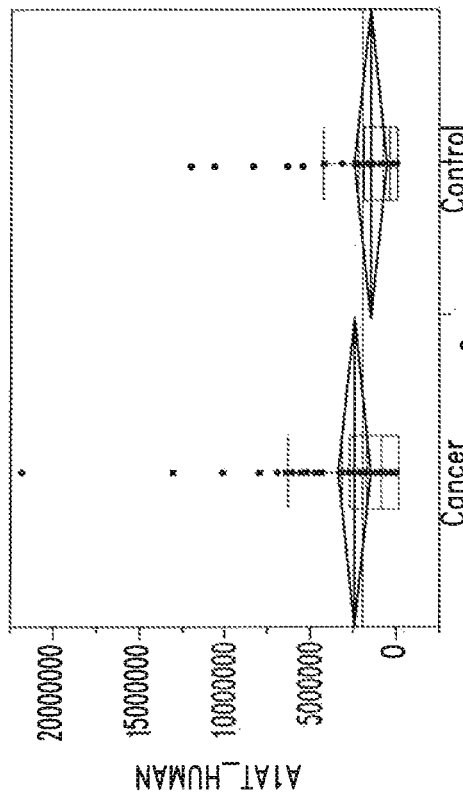
Figure 4E:
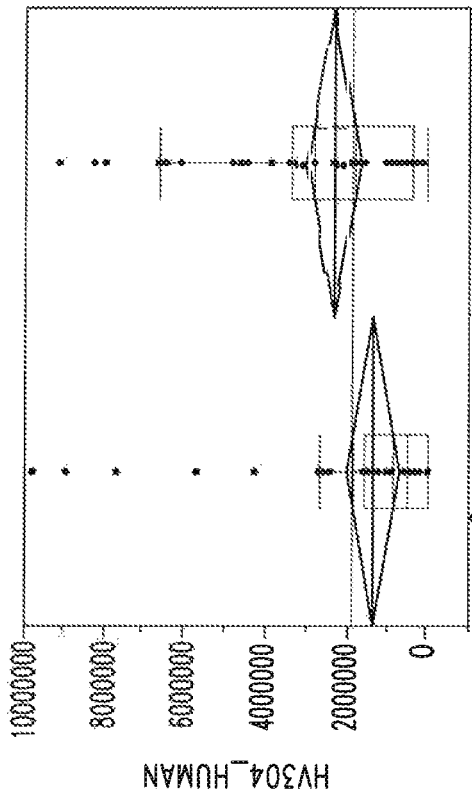
Figure 4F:
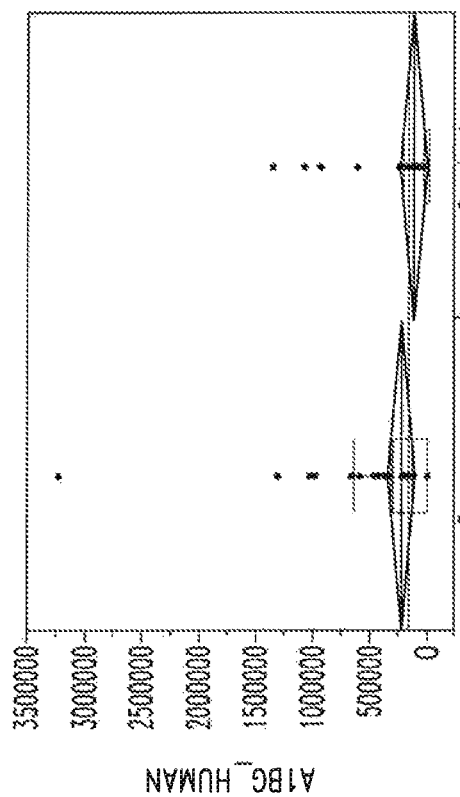

Experiment 1: Out of the 75 samples tested, breast density scores were obtained for 41 of the samples. The break down of the sample population by breast density was 14% category 1, 36.6% category 2, 43.9% category 3, 4.7% category 4 (FIG. 2). Eighteen of the twenty-five cancer samples were collected from patients diagnosed with Intra ductal carcinoma (IDC). Two patients were diagnosed with ductal carcinoma In Situ (DCIS), one patient was diagnosed with lobular carcinoma In Situ (LCIS), and one patient was diagnosed with intra lobular carcinoma (ILC).

For classification a scale was designed where a classification of "small" was given to tumors <20 mm, a classification of "medium" was assigned to tumors between 21 mm-99 mm, and a classification of "large" was assigned to tumors >1 cm. Seventeen of the samples collected from breast cancer patients were classified as large tumors, two samples were classified as medium, and six were classified as small. Pathology information of receptor type was obtained for eight of the cancer samples. One sample was ER−/HER2−, one sample was ER−/PR−, two samples were ER+/HER2−, three samples were ER+/HER2+, and one sample was ER+/PR−.

Figure 10:
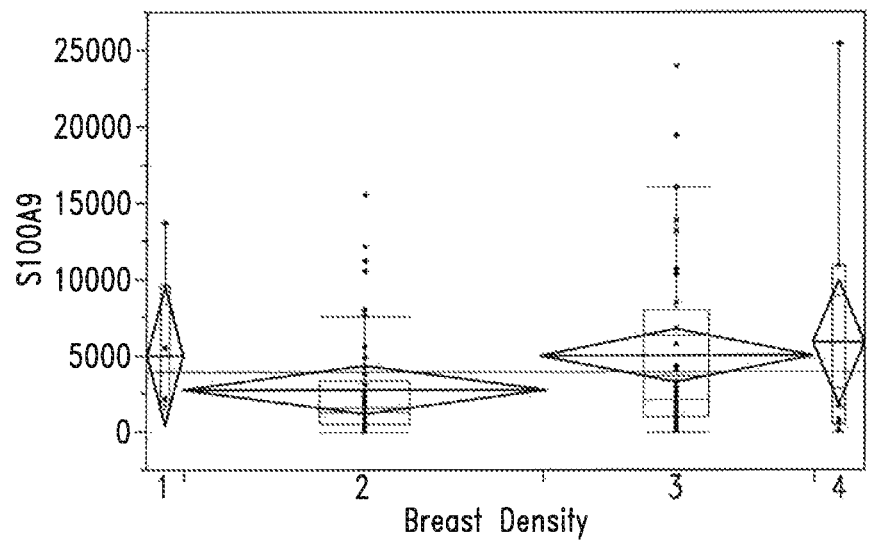
FIG. 10: ANOVA for S100A9 expression based on breast tissue category.
Figure 11:
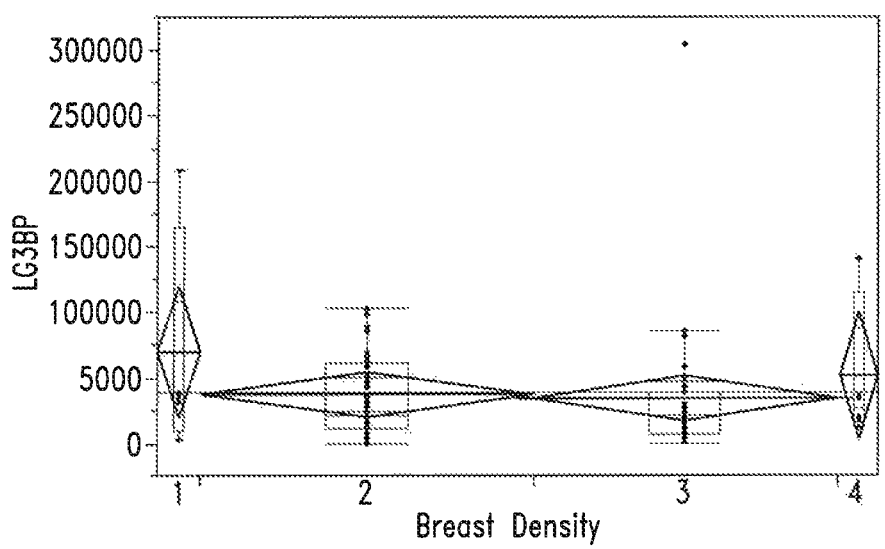
FIG. 11 ANOVA of LG3BP expression based on breast tissue category.

Experiment 2: The sample pool analyzed in this study consisted of 5.9% category 1 breast tissue; 50% category 2; 37.8% category 3, and 5.4% category 4. ANOVA analysis was conducted on several proteins evaluated by ELISA to determine if breast tissue type affects protein expression levels. Representative data is provided for two proteins studied (FIG. 10 and FIG. 11). Using an alpha level of 0.05, no statistically significant difference was observed for the means of the four types of breast tissue for each of the proteins evaluated in the ELISAs shown in FIGS. 10 and 11.

Samples were collected from a variety of breast cancer types resulting in 17 samples from patients diagnosed with DCIS, 44 samples from patients diagnosed with IDC, 4 samples from patients with both DCIS & IDC, and 5 samples from patients with ILC. Tumor size varied tremendously. Using that classification system described for Experiment 1, for the samples where tumor size was provided, 33 samples from patients with large tumors were tested, 9 samples from patients with medium tumor size, and 12 samples from patients with small tumor size. Of the 38 samples where receptor type was provided 1 sample was ER−, 2 samples were ER−/HER2−, 2 samples were triple negative (ER−/HER2−/PR−), 1 sample was ER−/HER2+, 11 samples were ER+, ER+/HER2 16, and 5 samples were ER+/HER2+. To date no distinguishing trend has been observed based on tumor size, cancer type, or receptor status, for the proteins that have been studied.

REFERENCES

Armstrong, K., Handorf, E. A., Chen, J., & Bristol Demeter, M. N. (2013). Breast cancer risk prediction and mammography biopsy decisions: a model-based study. *Ameri-* can *Journal of Preventive Medicine,* 44(1), 15-22. doi: 10.1016/j.amepre.2012.10.002

Bigenwald, R. Z., Warner, E., Gunasekara, A., Hill, K. A., Causer, P. A., Messner, S. J., Eisen, A., Plewes, D. B., Narod, S. A., Zhang, L., Yaffe, M. J. (2008) Is Mammography Adequate for Screening Women with Inherited BRCA Mutations and Low Breast Density?. Cancer Epidemiology Biomarkers Prevention, 17(3); 707-711.

Böhm, D., Keller, K., Pieter, J., Boehm, N., Wolters, D., Siggelkow, W., et al. (2012). Comparison of tear protein levels in breast cancer patients and healthy controls using a de novo proteomic approach. *Oncology Reports,* 28(2), 429-438. doi:10.3892/or.2012.1849

Böhm, D., Keller, K., Wehrwein, N., Lebrecht, A., Schmidt, M., Kölbl, H., &-Grus, F.-H. (2011). Serum proteome profiling of primary breast cancer indicates a specific biomarker profile. *Oncology Reports,* 26(5), 1051-1056. doi:10.3892/or.2011.1420

Boyd, N. F, Guo, H., Martin, L. J., Sun, L., Stone, J., Fishell, E., Jong, R. A., Hislop, G., Chiarelli, A., Minkin, S., Yaffee, M. J., (2007) Mammographic Density and the Risk and Detection of Breast Cancer. *The New England Journal of Medicine.* 356(3): 227-236).

Brown, M. L., Houn, F., Sickles, E. A., & Kessler, L. G. (1995). Screening Mammography in Community Practice: Positive Predictive. *American Journal of Radiology,* 165, 1373-1377.

CLIA Laws and Regulations, 2013, http://wwwn.cdc.gov/CLIA/Regulatory/default.aspx.

Grady, D. (2012). Study of Breast Biopsies Finds Surgery Used Too Extensively. *New York Times,* 1-4.

Klifa, C., Carballido-Gamio, J., Wilmes, L., Laprie, A., Shepherd, J., Gibbs, J., Fan, B., Noworolski, S., Hylton, N. (2010) Magnetic resonance imaging for secondary assessment of breast density in a high-risk cohort. *Magnetic Resonance Imaging.* 28; 8-15.

Kolb; T., Lichy, J., & Newhouse, J. (2002). Comparison of the performance of screening mammography, physical examination, and breast US and evaluation of factors that influence them: an analysis of 27,825 patient evaluations. *Radiology,* 225(1), 165-175.

Lebrecht, A., Boehm. D., Schmidt. M., Koelbl, H., & Grus, F. H. (2009a). Surface-enhanced Laser Desorption/Ionisation Time-of-flight Mass Spectrometry to Detect Breast Cancer Markers in Tears and Serum. *Cancer Genomics & Proteomics,* 6(2), 75-83.

Lebrecht, A., Boehm, D., Schmidt, M., Koelbl, H., Schwirz, R. L., & Grus, F. H. (2009b). Diagnosis of breast cancer by tear proteomic pattern. *Cancer Genomics & Proleomics,* 6(3), 177-182.

Li, J., Zhang, Z., Rosenzweig, J., Wang, Y., & Chan, D. (2002). Proteomics and bioinformatics approaches for identification of serum biomarkers to detect breast cancer. *Clin Chem,* 48(8), 1296-1304.

Luftner, D., & Possinger, K. (2002). Nuclear matrix proteins as biomarkers for breast cancer. *Expert Rev Mol Diagn,* 2(1), 23-31. doi:ERM020106 [pii] 10.1586114737159.2.1.23

Pisano, E. D., Gatsonis, C., Hendrick E., Yaffe, M., Baum, J. K., Acharyya, S., Conant, E. F. Fajardo, L. L., Bassett, L., D'Orsi, C. Jong, R., Rebner., M. (2005). Diagnostic Performance of Digital versus Film Mammography for Breast-Cancer Screening. *The New England Journal of Medicine.* 17(353), 1773-1783.

Scheel, J. R., Lee, J. M., Sprague, B. L., Lee, C. I., Lehman, C. D. (2015) Screening ultrasound as an adjunct to mammography in women with mammographically dense breasts. *Gynecology.* 212(1); 9-17.

Schiess, R., Wollscheid, B., & Aebersold, R. (2009). Targeted proteomic strategy for clinical biomarker discovery. *Molecular Oncology,* 3(1), 33-44. doi:10.1016/j.molonc.2008.12.001

Tabor, L., Vitak, B., Chen, T. H., Yen, A. M., Cohen, A., Tot, T., Chiu, S., Chen, S. Fann, J. Rosell, J., Fohlin, H., Smith, R. A., Duffy, S. W., (2011) Swedish Two-County Trial: Impact of Mammographic Screening on Breast Cancer Mortality during 3 Decades. *Radiology,* 3(260), 658-663.

Vachon, C. M., van Gils, C. H., Sellers, T. A., Ghosh, K., Pruthi, S., Brandt, K. R., Pankratz, V. S., (2007) Mammographic density, breast cancer risk and risk prediction. *Breast Cancer Research* 9:2017 (doi:10.1186/bcr1829).

Wu, K., & Zhang, Y. (2007). Clinical application of tear proteomics: Present and future prospects. *Proteomics. Clinical Applications.* 1(9), 972-982.

APPENDIX 1

| Protein Name | UniProt | IPI | Gene Name |
|---|---|---|---|
| Lipocalin 1 | P10325 | | LCN1_Human |

Trypsin Fragments

| | | |
|---|---|---|
| 1. QSETCSPGSD (SEQ ID NO: 1) | 2. VTMLISGR (SEQ ID NO: 2) | 3. AVLEKTDEPGK (SEQ ID NO: 3) |
| 4. AVLEKTDEPGKYTADGGK (SEQ ID NO: 4) | 5. TDEPGKYTADGGK (SEQ ID NO: 5) | 6. HVAYIIR (SEQ ID NO: 6) |
| 7. DPKNNLEALEDFEK (SEQ ID NO: 7) | 8. SHVKDHYTFYCEGELHGKPVR (SEQ ID NO: 8) | 9. DHYIFYCEGELHGKPVR (SEQ ID NO: 9) |
| 10. SHVKDHYIFYCEGELHGK (SEQ ID NO: 10) | 11. LVGRDPKNNLEALEDFEK (SEQ ID NO: 11) | 12. GLSTESILIPR (SEQ ID NO: 12) |
| 13. NNLEALEDFEKAAGAR (SEQ ID NO: 13) | 14. YTADGGKHVAYIIR (SEQ ID NO: 14) | 15. AAGARGLSTESILIPR (SEQ ID NO: 15) |
| 16. TDEPGKYTADGGKHVAYIIR (SEQ ID NO: 16) | 17. AAGARGLSTESILIPRQSETCSPGSD (SEQ ID NO: 17) | 21. DHYIFYCEGELHGK (SEQ ID NO: 18) |

APPENDIX 1-continued

| 19. NNLEALEDFEK (SEQ ID NO: 19) | 20. AMTVDREFPEMNLESVTPMTLTTLEGGN (SEQ ID NO: 20) | 21. GLSTESILIPRQSETCSPGSD (SEQ ID NO: 21) |

Proteins selected throught Experiment 1:

(SEQ ID NO: 22)

```
        10          20          30          40          50          60
MKPLLLAVSL  GLIAALQAHH  LLASDEEIQD  VSGTWYLK20AM  TVDREFPEMN  LESVTPMTLT 70          80          90         100         110         120
TLEGGNLEAK  *VTMLISGRCQ  EVK3,4AVLEK5,16TD  EPGK14YTADGG  K6HVAYIIR8SH  VK9,10,18DHYIFYCE 130         140         150         160         170
GELHGKPVRG  VK11LVGR7DPK13,19N  NLEALEDFEK  15,17AAGAR12,21GLSTE  SILIPR1QSET  CSPGSD
```

| Protein Name | UniProt | IPI | Gene Name |
|---|---|---|---|
| Zinc-α-glycoprotein | P25311 | | ZA2G_Human |

Trypsin Fragments

| 1. AGVQEPELR (SEQ ID NO: 23) | 2. AYLEEECPATLR (SEQ ID NO: 24) | 3. CLAYDFYPGK (SEQ ID NO: 25) |
| 4. EIPAWVPFDPAAQITK (SEQ ID NO: 26) | 5. HVEDVPAFQALGSLNDLQFFR (SEQ ID NO: 27) | 6. LKCLAYDFYPGK (SEQ ID NO: 28) |
| 7. NILDRQDPPSVVVTSHQAPGEK (SEQ ID NO: 29) | 8. QDPPSVVVTSHQAPGEK (SEQ ID NO: 30) | 9. QKWEAEPVYVQR (SEQ ID NO: 31) |
| 10. WEAEPVYVQR (SEQ ID NO: 32) | 11. YSKNILDRQDPPSVVVTSHQAPGEK (SEQ ID NO: 33) | 12. YSLTYIYTGLSK (SEQ ID NO: 34) |
| 13. YYYDGKDYIEFNK (SEQ ID NO: 35) | 14. AYLEEECPATLRK (SEQ ID NO: 36) | 15. AKAYLEEECPATLRK (SEQ ID NO: 37) |
| 16. QVEGMEDWKQDSQLQK (SEQ ID NO: 38) | 17. CLAYDFYPGKIDVHWTR (SEQ ID NO: 39) | |

(SEQ ID NO: 40)

```
        10          20          30          40          50          60
MVRMVPVLLS  LLLLLGPAVP  QENQDGR12YSL  TVIYTGLSK13H  VEDVPAFQAL  GSLNDLQFFR 70          80          90         100         110         120
YNSKDRKSQP  MGLVR16QVEGM  EDWKQDSQLQ  KAREDIFMET  LKDIVEYYND  SNGSHVLQGR 130         140         150         160         170         180
FECEIENNRS  SGAFWK13YYYD  GKDYIEFNK8E  IPAWVPFDPA  AQITK9QK10WEA  EPVYVQR15AK2,18A 190         200         210         220         230         240
YLKEECPATL  RL11YLKYS5KNI  LDR8QDPPSVV  VTSHQAPGEK  KK6LK3,17CLAYDF  YPGKIDVHWT 250         260         270         280         290
R1AGVQEPEL  RGDVLHNGNG  TYQSWVVAV  PPQDTAPYSC  HVQHSSLAQP  LVVPWEAS
```

(SEQ ID NO: 41)

```
        10          20          30          40          50          60
1EVQLVESGGG  LVQPGGSLRL  SCAASGFTFS  YYNMNWVRQV  TGKGLEWVSA  IGTAGDQYYA 70          80          90         100         110         120
DSVKGRFTIS  RNDSKNTLYL  NMNSLR2AEDT  AVYYCARSPV  SLVDGWLYYY  YGSVWGQGTL
```

| Protein Name | UniProt | IPI | Gene Name |
|---|---|---|---|

(SEQ ID NO: 44)

```
            20          30          40          50          60
MSRSVALAVL  ALLSLSGLEA  IQRTPK6IQVY  SRHPAENGK2S  NFLNCYVSGF  HPSDIEVDLL 70          80          90         100         110
```

APPENDIX 1-continued

| Protein Name | UniProt | IPI | Gene Name |
|---|---|---|---|
| Ig heavy chain V-III region BRO | P01766 | | HV305_Human |

Trypsin Fragments

1. EVQLVESGGGLVQPGGSLR
(SEQ ID NO: 42)

2. AEDTAVYYCAR
(SEQ ID NO: 43)

3.

| | | | | |
|---|---|---|---|---|
| KEGER$^3$IEK$^4$VE | HSDLSFSKDW | SFYLLYYTEF | TPTEK$^6$DEYAC | R$^5$VNHVTLSQP | KIVKWDRDM |

| Protein Name | UniProt | IPI | Gene Name |
|---|---|---|---|
| Beta-2-microglobulin | P61769 | | B2MG_Human |

Trypsin Fragments

1. IQVYSRHPAENGK
(SEQ ID NO: 45)

2. SNFLNCYVSGFHPSDIEVDLLK
(SEQ ID NO: 46)

3. IEKVEHSDLSFSK
(SEQ ID NO: 47)

4. VEHSDLSFSK
(SEQ ID NO: 48)

5. VNHVTLSQPK
(SEQ ID NO: 49)

6. DEYACRVNHVTLSQPK
(SEQ ID NO: 50)

(SEQ ID NO: 51)

| | 20 | 30 | 40 | 50 | 60 |
|---|---|---|---|---|---|
| MKSSGLFPFL | VLLALGTLAP | WAVEGSKSF | K$^2$AGVCPPKKS | AQCLR$^4$YK$^6$KPE | CQSDWQCPGK |
| 70 | 80 | 90 | 100 | 110 | 120 |
| KR$^2$CCPDTCGI | K$^3$CLDPVDTPN | PTRRKPGKCP | VTYGQCLMLN | PPNFCEMDGQ | CKRDLKCCMG |
| 130 | | | | | |
| MCGK$^6$SCVSPV | KA | | | | |

| Antileukoproteinase | P03972 | | SLP1_Human |
|---|---|---|---|

Trypsin Fragments

1. AGVCPPKKSAQCLR
(SEQ ID NO: 52)

2. CCPDTCGIKCLDPVDTPNPTR
(SEQ ID NO: 53)

3. CLDPVDTPNPTR
(SEQ ID NO: 54)

4. VHVGDEDFVHLR
(SEQ ID NO: 55)

5. SCVSPVKA
(SEQ ID NO: 56)

6. KPECQSDWQCPGK
(SEQ ID NO: 57)

(SEQ ID NO: 60)

| 10 | 20 | 30 | 40 | 50 | 60 |
|---|---|---|---|---|---|
| MEFGLSWLFL | VAILKGVQC$^1$E | VQLLESGGGL | VQPGGSLRLS | CAASGFTFSS | YAMSWVRQAF |
| 70 | 80 | 90 | 100 | 110 | |

| Protein Name | UniProt | IPI | Gene Name |
|---|---|---|---|
| Ig Heavy Chain V-III VH26 | P01764 | | LV303_Human |

Trypsin Fragments

1. EVQLLESGGGLVQPGGSLR
(SEQ ID NO: 58)

2. AEDTAVYYCAK
(SEQ ID NO: 59)

3.

| | | | | |
|---|---|---|---|---|
| GKGLEWVSAI | SGSGGSTYYG | DSVKGRFTIS | RDNSKNTLYL | QMNSLR$^2$AEDT | AVYYCAK |

| Protein Name | UniProt | IPI | Gene Name |
|---|---|---|---|
| Cystatin-B | P04080 | | CYTN_Human |

Trypsin Fragments

1. AVSFSQVVAGTNFIK
(SEQ ID NO: 61)

2. SQVVAGTNYFIK
(SEQ ID NO: 62)

3. VFQSLPHENKPLETLSNYQTNK
(SEQ ID NO: 63)

4. VHVGDEDFVHLR
(SEQ ID NO: 64)

(SEQ ID NO: 65)

| 10 | 20 | 30 | 40 | 50 | 60 |
|---|---|---|---|---|---|
| MMCGAPSATQ | PATAETQHIA | DQVRSQLEEK | ENKKFPVFK$^2$A | VSFK$^2$SQVVAG | TNYFIK$^4$VHVG |
| 70 | 80 | 90 | | | |
| DEDFVHLR$^4$VF | QSLPHENKPL | TLSNYQTNKA | KHDELTYF | | |

APPENDIX 1-continued

| Protein Name | UniProt | IPI | Gene Name |
|---|---|---|---|
| Ig Lambda Chain V-IV region HiL | P01717 | | LV403_Human |

Trypsin Fragments

1. SYELTQPPSVSVSPGQTAR (SEQ ID NO: 66)
2.
3.

(SEQ ID NO: 76)

```
      10          20          30          40          50          60
SYELTQPPSV  SVSPGQTARI  TCSANALPNQ  YAYWYQQKPG  RAPMVIYKD   TQRPSGIPQR
```

| Protein Name | UniProt | IPI | Gene Name |
|---|---|---|---|
| Galectin-3 | P17931 | | LEG3_Human |

Trypsin Fragments

1. IQVLLVEPDHFK (SEQ ID NO: 67)
2. QSVFPFESGKPFK (SEQ ID NO: 68)
3. VIVCNTKLDNNWGR (SEQ ID NO: 69)

4. IALDFQR (SEQ ID NO: 70)
5. VAVNDAHLLQYNHR (SEQ ID NO: 71)
6. GNDVAFHFNPR (SEQ ID NO: 72)

7. MLITILGTVKPNANR (SEQ ID NO: 73)
8. RVIVCNTKLDNNWGR (SEQ ID NO: 74)
9. KLNEISK (SEQ ID NO: 75)

```
     70          80          90         100
FSSSTSGTTV  TLTISGVQAE  DEADYYCQAW  DNSASIFGGG  TKLTVLG
```

(SEQ ID NO: 77)

```
      10          20          30          40          50          60
MADNFSLHDA  LSGSGNPNPQ  GWPGAWGNQP  AGAGGYPGAS  YPGAYPGQAP  PGAYPGQAPP
      70          80          90         100         110         120
GAYPGAPGAY  PGAPAPGVYP  GPPSGPGAYP  SSGQPSATGA  YPATGPYGAP  AGPLIVPYNL
     130         140         150         160         170         180
PLPGGVVPR⁷M  LITILGTVKP  NANR⁴IALDFQ  R⁴GNDVAFHFN  PRFNENNR³R³V  IVCNTKLDNN
     190         200         210         220         230         240
WGREER²QSVF  PFESGKPFK¹I  QVLVEPDHFK  ²VAVNDAHLLQ  YNHRVK⁹KLNE  ISKLGISGDI
     250
DLTSASYTMI
```

(SEQ ID NO: 78)

```
      10          20          30          40          50          60
M¹AGELTPEEE  AQYK²K³AFSAV  DTDGNGTINA  QELGAALKAT  GK⁸NLSEAQLR  KLISEVDSDG
      70          80          90         100         110         120
DGEISFQEFL  TAAKKAR⁴AGL  EDLQVAFRAF  DQDGDGHITV  DELRRAMAGL  GQPLPQEELD
     130         140
AMIR⁵EADVDQ  DGRVNYEEFA  RMLAQE
```

Protein selected from Experiment 2:

| Protein Name | UniProt | IPI | Gene Name |
|---|---|---|---|
| Calmodulin-like protein 5 | Q9NZT1 | | CALL5_Human |

Trypsin Fragments

1. AGELTPEEAQYKK (SEQ ID NO: 79)
2. KAFSAVDTDGNGTINAQELGAALK (SEQ ID NO: 80)
3. AFSAVDTDGNGTINAQELGAALK (SEQ ID NO: 81)

4. AGELDLQVAFR (SEQ ID NO: 82)
5. EADVDQDGRVNYEEFAR (SEQ ID NO: 83)
6. NLSEAQLR (SEQ ID NO: 84)

TABLE 1

| Protein Name | Gene | Protein Name | Gene |
|---|---|---|---|
| Ig lambda chain V-IV region Hil | LV403 | 60S acidic ribosomal protein P1 | RLA1 |
| Ig heavy chain V-III BRO | HV305 | Inter-alpha-frypsin inhibitor heavy chain H2 | ITIH2 |
| Ig heavy chain V-III VH26 | HV303 | Mucin-like protein 1 | MUCL1 |
| Beta-2-microglobulin | B2MG | S100 A6 | S10046 |
| Lipocalin-1 | LCN1 | Na(+)/H(+) exchange regulatory cofactor NHE-RP1 | NHRP1 |
| Zinc-α-2-glycoprotein | ZA2G | Thioredoxin domain-containing protein 17 | I3L0K2 |
| Cystatin B | CYTB | Lymphocyte-specific protein | LSP1 |
| Antileukoproteinase | SLP1 | Cluster of Haptoglobin | H3BS21 |
| Galectin-3 | LEG3 | Myosin regulatory light chain 12A | J2QRS3 |
| Histidine triad nucleotide-binding protein 1 | D6RD60 | Ribonuclease inhibitor | RINI |
| S100A9 | S1049 | Alpha-enolase | ENOA |
| S100A8 | S10AS | Cluster of Ig kappa chain V-I region EU | KV106 |
| Galectin-3-binding protein | LG3BP | Alcohol dehydrogenase class 4 mu/sigma chain | ADH7 |
| Cluster of Ig alpha-1 chain C region | IGHA1 | Protein AMBP | AMBP |
| Cluster of Ig kappa chain V-III region HAH | KV312 | Angiotensinogen | ANGT |
| VEGF co-regulated chemokine 1 | VCC1 | Antithrombin-III | ANT3 |
| L-lactate dehydrogenase A chain | LDHA | Apolipoprotein A-II | APOA2 |
| Aldo-keto reductase family 1 member C | AKRIC1 | Calpastatin | B7Z574 |
| Rootletin | B1AKD8 | Brain acid soluble protein 1 | BASP1 |
| L-lactate dehydrogenase B chain | LDHB | Alpha-2-HS-glycoprotein | C9JV77 |
| Retinal dehydrogenase 1 | ALIA1 | Calreticulin | CALR |
| Uncharacterized Protein | B4EIZ4 | Calpain-l catalytic subunit | CAN1 |
| Alpha-1-antichymotrypsin | AACT | Cell division control protein 42 homolog | CDC42 |
| Superoxide dismutase [Cn-Zn] | SODC | Complement C3 | CO3 |
| SPARC-like protein 1 | SPRL1 | Coronin-1A | COR1A |
| Ig heavy chain V-III region TIL | HV304 | Programmed cell death 6-interacting protein | DCD |
| Keratin | K1C9 | Definsin 1 | DEF1 |
| Cystatin-SN | CYTN | P-box only protein 50 | PBX50 |
| Alpha-actinin-4 | ACTN4 | Gamma-glutamylcyclotransferase | GGCT |
| Ig lambda-3 chain C regions (Fragment) | IGLC3 | Glutathione reductase, mitochondrial | GSHR |
| Immunoglobulin lambda-like polypeptide 5 | IGLL5 | Keratin, type II cytoskeletal I | K2C1 |
| Alcohol dehydrogenase 1C | ADHIG | UMP-CMP kinase | KCY |
| Malate dehydrogenase, mitochondrial | MDHM | Mesothelin | MSLN |
| Calmodulin-like protein 5 | CALL5 | N-acetylmuramoyl-L-alanine amidase | PGRP2 |
| Alpha-1-antitrypsin | A1AT | Nicotinate phosphotibosyltransferase | PNCB |
| Alpha-1B-glycoprotein | A1BG | Inter-alpha-trypsin inhibitor heavy chain H1 | ITIH1 |
| Leucine-rich alpha-2-glycoprotein | A2GL | Ribonuclease T2 | RNASET2 |
| Small ubiquitin-relaed modifier 3 | A8MU27 | Superoxide dismutase [Mn], mitochondrial | SODM |
| Anterior gradient protein 2 homolog | AGR2 | Small proline-rich protein 3 | SPRR3 |
| Profilin-1 | PRGFI | Src substrate corinctin | SRC8 |
| Cluster of Ig lambda chain V-III region LOI | LV302 | Cluster of Tubulin beta-4B chain | TBB4B |
| Prothrombin | E9PIT3 | Tropomyosin alpha-3 chain | TPM3 |
| Hemopexin | HEMO | Serotransferrin | TRFE |
| Ig gamma-2 chain C region | IGHG2 | Glutathione S-transferase P | THIO |
| Ubiquitin-40S ribosomal protein S27a | RPS27A | Vitronectin | VTNC |
| Afamin | AFAM | Vitamin D Binding protein | Q6LDC6 |
| Apolipoprotein A-I | APOA1 | Inter-alpha-trypsin inhibitor heavy chain H4 | ITIH4 |
| Apolipoprotein A-IV | APOA4 | Metalloprotease inhibitor | TIMP1 |
| Flavin reductase (NADPH) | BLVRB | Heat Shock protein 90 | HSP90 |
| Prosaposin | PSAP | Cathepsin B | CATB |
| Lactitin | LACRT | Ceruloplasmin | CERU |
| 14-3-3 sigma | 1433S | Calprotectin | |
| alpha-2-hs-glycoprotein | FETUA | alpha-2-macroglobulin | A2MG |
| | | Transthyretin | TTHY |

---

What is claimed is:

1. A method of treating breast cancer in a subject, comprising: obtaining a sample of lacrimal secretions from the subject; detecting levels in the sample of at least one marker comprising S100-A11; determining the subject has breast cancer when the levels of S100-A11 are decreased as compared to the levels in a control sample lacking breast cancer; and administering an appropriate anti-cancer therapeutic to the subject when the subject is determined to have breast cancer.

2. The method of claim 1, wherein the subject is a human.

3. The method of claim 1, wherein the S100-A11 marker is decreased at least, 1.5 fold, 2 fold, 4 fold or more relative to the level of the marker in the control sample.

4. The method of claim 1, wherein a combination of markers are used to determine the likelihood of cancer in the subject.

5. The method of claim 1, wherein the level of the marker is detected by liquid chromatography-mass spectroscopy (LC-MS).

6. The method of claim 1, wherein the level of the marker is detected by an antibody-based detection method.

7. The method of claim 1, wherein the level of the marker is detected by multiplex protein detection method.

8. The method of claim 1, wherein the level of the marker is detected by an mRNA detection method.

9. The method of claim 1, wherein the subject is suspected of having cancer.

10. The method of claim 1, wherein the subject is at increased risk for developing a cancer.

11. The method of claim 1, wherein the subject has a palpable lump suspected of being cancerous.

12. The method of claim 1, wherein the breast density of the subject is category 1, category 2, category 3 or category 4.

13. The method of claim 1, wherein the cancer is detected as a stage of breast cancer.

14. The method of claim 1, wherein at least ten markers are used in combination.

15. The method of claim 1, wherein at least five markers are used in combination.

16. The method of claim 1, wherein at least three markers are used in combination.

* * * * *